(12) United States Patent
Fathieh et al.

(10) Patent No.: US 12,324,683 B2
(45) Date of Patent: Jun. 10, 2025

(54) METHOD AND SYSTEM FOR ENGINEERING CYCLE VARIABILITY-RELATED FEATURES FROM BIOPHYSICAL SIGNALS FOR USE IN CHARACTERIZING PHYSIOLOGICAL SYSTEMS

(71) Applicant: Analytics for Life Inc., Toronto (CA)

(72) Inventors: Farhad Fathieh, North York (CA); Timothy William Fawcett Burton, Ottawa (CA)

(73) Assignee: Analytics for Life Inc., Toronto (CA)

( * ) Notice: Subject to any disclaimer, the term of this patent is extended or adjusted under 35 U.S.C. 154(b) by 273 days.

(21) Appl. No.: 17/558,702

(22) Filed: Dec. 22, 2021

(65) Prior Publication Data

US 2022/0192596 A1 Jun. 23, 2022

Related U.S. Application Data

(60) Provisional application No. 63/130,324, filed on Dec. 23, 2020.

(51) Int. Cl.
*A61B 5/00* (2006.01)
*A61B 5/021* (2006.01)
*G16H 50/20* (2018.01)

(52) U.S. Cl.
CPC ............ *A61B 5/4842* (2013.01); *A61B 5/021* (2013.01); *A61B 5/7264* (2013.01); *A61B 5/742* (2013.01); *G16H 50/20* (2018.01)

(58) Field of Classification Search
CPC ... A61B 5/7264; A61B 5/7267; A61B 5/7282; A61B 5/7275; A61B 5/021;
(Continued)

(56) References Cited

U.S. PATENT DOCUMENTS

| | | | |
|---|---|---|---|
| 2014/0257122 A1* | 9/2014 | Ong ................... | A61B 5/316 705/2 |
| 2016/0378936 A1* | 12/2016 | Burton ................ | A61B 5/316 600/509 |

(Continued)

OTHER PUBLICATIONS

Mielniczuk, L.M. et. al, (2007), Left Ventricular End-Diastolic Pressure and Risk of Subsequent Heart Failure in Patients Following an Acute Myocardial Infarction. Congestive Heart Failure, 13: 209-214. doi.org/10.1111/j.1527-5299.2007.06624.x (Year: 2007).*

(Continued)

*Primary Examiner* — Jennifer Robertson
*Assistant Examiner* — Elina Sohyun Jang
(74) *Attorney, Agent, or Firm* — Meunier Carlin & Curfman LLC

(57) ABSTRACT

The exemplified methods and systems facilitate the use, for diagnostics, monitoring, or treatment, of one or more cycle variability based features or parameters determined from biophysical signals such as cardiac or photoplethysmography signals that are acquired non-invasively from surface sensors placed on a patient while the patient is at rest. The estimated metric may be used to assist a physician or other healthcare provider in diagnosing the presence or non-presence and/or severity and/or localization of diseases or conditions or in the treatment of said diseases or conditions.

18 Claims, 16 Drawing Sheets

(58) Field of Classification Search
CPC ............ A61B 5/02405; A61B 5/02416; A61B 5/1102; A61B 5/346; A61B 5/366; A61B 5/02028; A61B 5/02; A61B 5/04012; A61B 5/042; A61B 5/24; A61B 5/283; A61B 5/316; A61B 5/4848; A61B 5/725; A61B 5/7257; A61B 5/7278; A61B 5/341; A61B 5/6801; A61B 5/681; A61B 5/6823; A61B 5/6824; A61B 5/7203; A61B 5/4842; A61B 5/742; A61B 5/0022; A61B 5/349; A61B 5/369; A61B 5/7221; A61B 5/02007; A61B 5/024; A61B 5/242; G16H 50/20; G16H 50/30; G16H 50/70; G06F 19/345; G06F 16/285; G06F 18/23; Y02A 90/10
See application file for complete search history.

(56) References Cited

U.S. PATENT DOCUMENTS

| | | |
|---|---|---|
| 2018/0177415 A1 | 6/2018 | Madl |
| 2019/0104951 A1 | 4/2019 | Valys et al. |
| 2019/0384757 A1* | 12/2019 | Garrett ................. A61B 5/7221 |
| 2020/0229713 A1 | 7/2020 | Gopalakrishn et al. |

OTHER PUBLICATIONS

Written Opinion Of The International Searching Authority in PCT/IB2021/062193 (Apr. 7, 2022).
European Search Report dated Oct. 15, 2024 for Application No. 21909687.2.

* cited by examiner

METHOD AND SYSTEM FOR ENGINEERING CYCLE VARIABILITY-RELATED FEATURES FROM BIOPHYSICAL SIGNALS FOR USE IN CHARACTERIZING PHYSIOLOGICAL SYSTEMS

This application claims priority to, and the benefit of, U.S. Provisional Patent Application No. 63/130,324, filed Dec. 23, 2020, entitled "Method and System to Assess Disease Using Cycle Variability Analysis of Biophysical Signals," which is incorporated by reference herein in its entirety.

FIELD OF THE INVENTIONS

The present disclosure generally relates to methods and systems for engineering features or parameters from biophysical signals for use in diagnostic applications; in particular, the engineering and use of cycle variability-related features for use in characterizing one or more physiological systems and their associated functions, activities, and abnormalities. The features or parameters may also be used for monitoring or tracking, controls of medical equipment, or to guide the treatment of a disease, medical condition, or an indication of either.

BACKGROUND

There are numerous methods and systems for assisting a healthcare professional in diagnosing disease. Some of these involve the use of invasive or minimally invasive techniques, radiation, exercise or stress, or pharmacological agents, sometimes in combination, with their attendant risks and other disadvantages.

Diastolic heart failure, a major cause of morbidity and mortality, is defined as symptoms of heart failure in a patient with preserved left ventricular function. It is characterized by a stiff left ventricle with decreased compliance and impaired relaxation leading to increased end-diastolic pressure in the left ventricle, which is measured through left heart catheterization. Pulmonary hypertension (PH) generally refers to high blood pressure in the arteries of the lungs and can include a spectrum of conditions. The current clinical standard of care for PH, and for pulmonary arterial hypertension (PAH), in particular, involves a cardiac catheterization of the right side of the heart that directly measures the pressure in the pulmonary arteries. CAD can occur when the lining inside the coronary arteries that supply blood to the myocardium, or heart muscle, develops atherosclerosis (the hardening or stiffening of the lining and the accumulation of plaque therein, often accompanied by abnormal inflammation). Coronary angiography is the current standard of care used to assess coronary arterial disease (CAD) as determined through the coronary lesions described by a treating physician. Non-invasive imaging systems such as magnetic resonance imaging and computed tomography require specialized facilities to acquire images of blood flow and arterial blockages of a patient that are reviewed by radiologists.

It is desirable to have a system that can assist healthcare professionals in the diagnosis of cardiac disease and various other diseases and conditions without the aforementioned disadvantages.

SUMMARY

A clinical evaluation system and method are disclosed that facilitate the use of one or more cycle variability-related features or parameters determined from biophysical signals such as cardiac/biopotential signals and/or photoplethysmography signals that are acquired, in preferred embodiments, non-invasively from surface sensors placed on a patient while the patient is at rest. Cycle variability refers to variations in the cardiac cycle (such as amplitudes and/or durations in the cardiac waveforms), or spectral or information content that is in-band to the frequency range of the cardiac signal and has a similar amplitude, but is not synchronized with the cardiac cycle. Cycle variability can be used to detect muscle artifacts (e.g., skeletal muscles), heart artifacts that are attributed to a pathology, or a state of disease or compliance, including those described herein. The cycle variability-related features or parameters can be used in a model or classifier (e.g., a machine-learned classifier) to estimate metrics associated with the physiological state of a patient, including for the presence or non-presence of a disease, medical condition, or an indication of either. The estimated metric may be used to assist a physician or other healthcare provider in diagnosing the presence or non-presence and/or severity and/or localization of diseases or conditions or in the treatment of said diseases or conditions.

The estimation or determined likelihood of the presence or non-presence of a disease, condition, or indication of either can supplant, augment, or replace other evaluation or measurement modalities for the assessment of a disease or medical condition. In some cases, a determination can take the form of a numerical score and related information.

In an aspect, the cycle variability properties of the biophysical signal may also be used to assess asynchronous motion (e.g., isometric contraction, electromyographic related movement, and other motion), to remove such motion, and associated signals, from the biophysical signal prior to analysis of the biophysical signal or for signal rejection.

Examples of cycle variability features include quantification of beat-to-beat variations in a time-series biophysical signal (e.g., biopotential signal) by comparing each beat to a calculated template beat. The template beat is a waveform represented across an entire acquired signal, or a subset of the acquired signal, and applying a median filter to the stacked beat-to-beat segmented signal, e.g., through ventricular depolarization (VD) peak matching.

As used herein, the term "feature" (in the context of machine learning and pattern recognition and as used herein) generally refers to an individual measurable property or characteristic of a phenomenon being observed. A feature is defined by analysis and may be determined in groups in combination with other features from a common model or analytical framework.

As used herein, "metric" refers to an estimation or likelihood of the presence, non-presence, severity, and/or localization (where applicable) of one or more diseases, conditions, or indication(s) of either, in a physiological system or systems. Notably, the exemplified methods and systems can be used in certain embodiments described herein to acquire biophysical signals and/or to otherwise collect data from a patient and to evaluate those signals and/or data in signal processing and classifier operations to evaluate for a disease, condition, or indicator of one that can supplant, augment, or replace other evaluation modalities via one or more metrics. In some cases, a metric can take the form of a numerical score and related information.

In the context of cardiovascular and respiratory systems, examples of diseases and conditions to which such metrics can relate include, for example: (i) heart failure (e.g., left-side or right-side heart failure; heart failure with preserved ejection fraction (HFpEF)), (ii) coronary artery disease (CAD), (iii) various forms of pulmonary hypertension (PH) including without limitation pulmonary arterial hypertension (PAH), (iv) abnormal left ventricular ejection fraction (LVEF), (v) hypertrophic cardiomyopathy, and various other diseases or conditions. An example indicator of certain forms of heart failure is the presence or non-presence of elevated or abnormal left-ventricular end-diastolic pressure (LVEDP). An example indicator of certain forms of pulmonary hypertension is the presence or non-presence of elevated or abnormal mean pulmonary arterial pressure (mPAP).

BRIEF DESCRIPTION OF THE DRAWINGS

The accompanying drawings, which are incorporated in and constitute a part of this specification, illustrate embodiments and, together with the description, serve to explain the principles of the methods and systems.

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION

Figure 1:
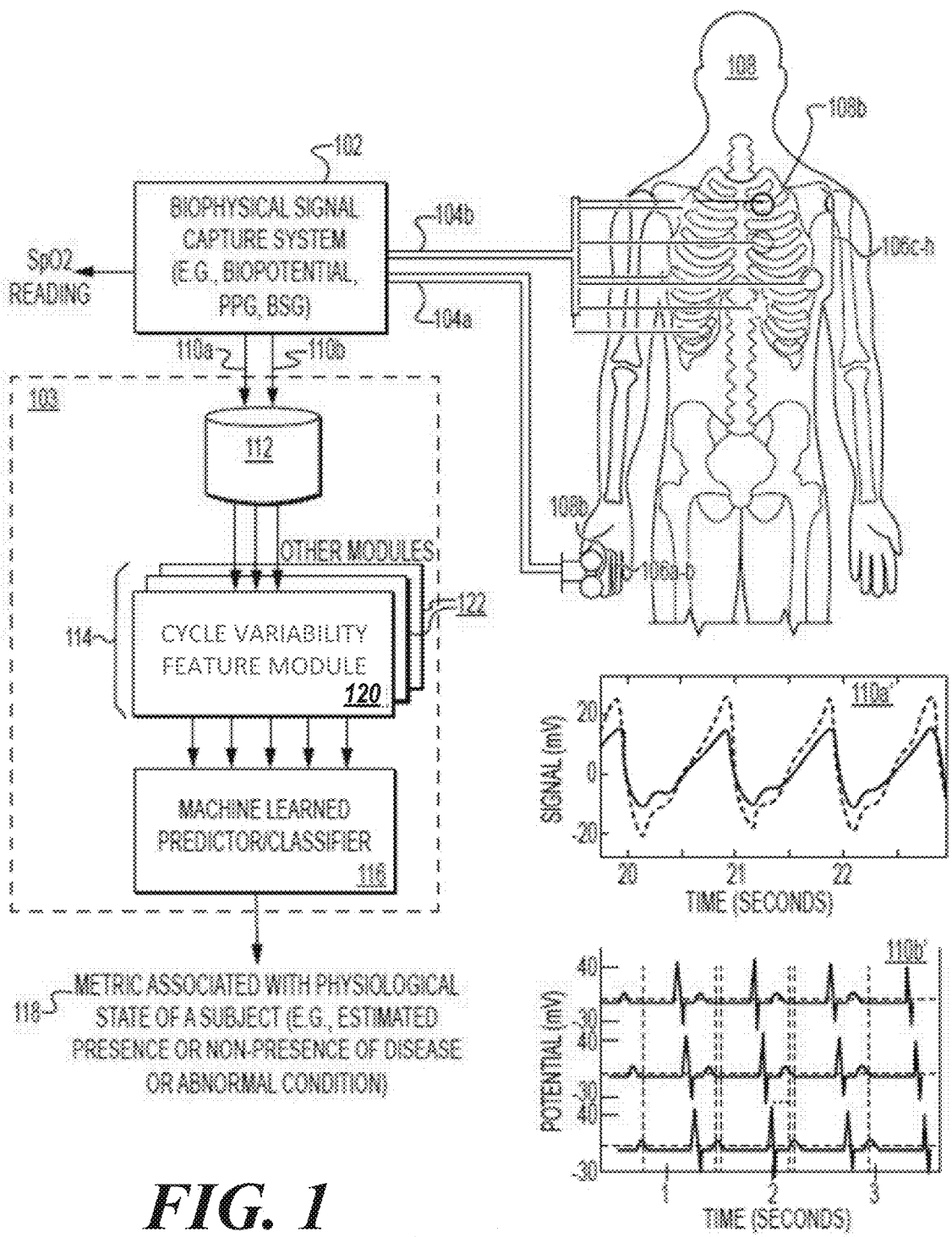
FIG. 1 is a schematic diagram of example modules, or components, configured to non-invasively compute cycle variability-related features or parameters to generate one or more metrics associated with the physiological state of a patient in accordance with an illustrative embodiment.

Each and every feature described herein, and each and every combination of two or more of such features, is included within the scope of the present invention provided that the features included in such a combination are not mutually inconsistent.

While the present disclosure is directed to the practical assessment of biophysical signals, e.g., raw or pre-processed photoplethysmographic signals, biopotential/cardiac signals, etc., in the diagnosis, tracking, and treatment of cardiac-related pathologies and conditions, such assessment can be applied to the diagnosis, tracking, and treatment (including without limitation surgical, minimally invasive, lifestyle, nutritional, and/or pharmacologic treatment, etc.) of any pathologies or conditions in which a biophysical signal is involved in any relevant system of a living body. The assessment may be used in the controls of medical equipment or wearable devices or in monitoring applications (e.g., to report cycle variability-related waveforms generated using the biophysical signals as disclosed therein).

The terms "subject" and "patient" as used herein are generally used interchangeably to refer to those who had undergone analysis performed by the exemplary systems and methods.

The term "cardiac signal" as used herein refers to one or more signals directly or indirectly associated with the structure, function, and/or activity of the cardiovascular system—including aspects of that signal's electrical/electrochemical conduction—that, e.g., cause contraction of the myocardium. A cardiac signal may include, in some embodiments, biopotential signals or electrocardiographic signals, e.g., those acquired via an electrocardiogram (ECG), the cardiac and photoplethysmographic waveform or signal capture or recording instrument later described herein, or other modalities.

The term "biophysical signal" as used herein includes but is not limited to one or more cardiac signal(s), neurological signal(s), ballistocardiographic signal(s), and/or photoplethysmographic signal(s), but it also encompasses more broadly any physiological signal from which information may be obtained. Not intending to be limited by example, one may classify biophysical signals into types or categories that can include, for example, electrical (e.g., certain cardiac and neurological system-related signals that can be observed, identified, and/or quantified by techniques such as the measurement of voltage/potential (e.g., biopotential), impedance, resistivity, conductivity, current, etc. in various domains such as time and/or frequency), magnetic, electromagnetic, optical (e.g., signals that can be observed, identified and/or quantified by techniques such as reflectance, interferometry, spectroscopy, absorbance, transmissivity, visual observation, photoplethysmography, and the like), acoustic, chemical, mechanical (e.g., signals related to fluid flow, pressure, motion, vibration, displacement, strain), thermal, and electrochemical (e.g., signals that can be correlated to the presence of certain analytes, such as glucose). Biophysical signals may in some cases be described in the context of a physiological system (e.g., respiratory, circulatory (cardiovascular, pulmonary), nervous, lymphatic, endocrine, digestive, excretory, muscular, skeletal, renal/urinary/excretory, immune, integumentary/exocrine and reproductive systems), one or more organ system(s) (e.g., signals that may be unique to the heart and lungs as they work together), or in the context of tissue (e.g., muscle, fat, nerves, connective tissue, bone), cells, organelles, molecules (e.g., water, proteins, fats, carbohydrates, gases, free radicals, inorganic ions, minerals, acids, and other compounds, elements, and their subatomic components. Unless stated otherwise, the term "biophysical signal acquisition" generally refers to any passive or active means of acquiring a biophysical signal from a physiological system, such as a mammalian or non-mammalian organism. Passive and active biophysical signal acquisition generally refers to the observation of natural or induced electrical, magnetic, optical, and/or acoustics emittance of the body tissue. Non-limiting examples of passive and active biophysical signal acquisition means include, e.g., voltage/potential, current, magnetic, optical, acoustic, and other non-active ways of observing the natural emittance of the body tissue, and in some instances, inducing such emittance. Non-limiting examples of passive and active biophysical signal acquisition means include, e.g., ultrasound, radio waves, microwaves, infrared and/or visible light (e.g., for use in pulse oximetry or photoplethysmography), visible light, ultraviolet light, and other ways of actively interrogating the body tissue that does not involve ionizing energy or radiation (e.g., X-ray). An active biophysical signal acquisition may involve excitation-emission spectroscopy (including, for example, excitation-emission fluorescence). The active biophysical signal acquisition may also involve transmitting ionizing energy or radiation (e.g., X-ray) (also referred to as "ionizing biophysical signal") to the body tissue. Passive and active biophysical signal acquisition means can be performed in conjunction with invasive procedures (e.g., via surgery or invasive radiologic intervention protocols) or non-invasively (e.g., via imaging, ablation, heart contraction regulation (e.g., via pacemakers), catheterization, etc.).

The term "photoplethysmographic signal" as used herein refers to one or more signals or waveforms acquired from optical sensors that correspond to measured changes in light absorption by oxygenated and deoxygenated hemoglobin, such as light wavelengths in the red and infrared spectra. Photoplethysmographic signal(s), in some embodiments, include a raw signal(s) acquired via a pulse oximeter or a photoplethysmogram (PPG). In some embodiments, photoplethysmographic signal(s) are acquired from off-the-shelf, custom, and/or dedicated equipment or circuitries that are configured to acquire such signal waveforms for the purpose of monitoring health and/or diagnosing disease or abnormal conditions. The photoplethysmographic signal(s) typically include a red photoplethysmographic signal (e.g., an electromagnetic signal in the visible light spectrum most dominantly having a wavelength of approximately 625 to 740 nanometers) and an infrared photoplethysmographic signal (e.g., an electromagnetic signal extending from the nominal red edge of the visible spectrum up to about 1 mm), though other spectra such as near-infrared, blue and green may be used in different combinations, depending on the type and/or mode of PPG being employed.

The term "ballistocardiographic signal," as used herein, refers to a signal or group of signals that generally reflect the flow of blood through the entire body that may be observed through vibration, acoustic, movement, or orientation. In some embodiments, ballistocardiographic signals are acquired by wearable devices, such as vibration, acoustic, movement, or orientation-based seismocardiogram (SCG) sensors, which can measure the body's vibrations or orientation as recorded by sensors mounted close to the heart. Seismocardiogram sensors are generally used to acquire "seismocardiogram," which is used interchangeably with the term "ballistocardiogram" herein. In other embodiments, ballistocardiographic signals may be acquired by external equipment, e.g., bed or surface-based equipment that measures phenomena such as a change in body weight as blood moves back and forth in the longitudinal direction between the head and feet. In such embodiments, the volume of blood in each location may change dynamically and be reflected in the weight measured at each location on the bed as well as the rate of change of that weight.

In addition, the methods and systems described in the various embodiments herein are not so limited and may be utilized in any context of another physiological system or systems, organs, tissue, cells, etc., of a living body. By way of example only, two biophysical signal types that may be useful in the cardiovascular context include cardiac/biopotential signals that may be acquired via conventional electrocardiogram (ECG/EKG) equipment, bipolar wide-band biopotential (cardiac) signals that may be acquired from other equipment such as those described herein, and signals that may be acquired by various plethysmographic techniques, such as, e.g., photoplethysmography. In another example, the two biophysical signal types can be further augmented by ballistocardiographic techniques.

FIG. 1 is a schematic diagram of example modules, or components, configured to non-invasively compute cycle variability-related features or parameters to generate, via a classifier (e.g., machine-learned classifier), one or more metrics associated with the physiological state of a patient in accordance with an illustrative embodiment. The modules or components may be used in a production application or the development of the cycle variability-related features and other classes of features.

The example analysis and classifiers described herein may be used to assist a healthcare provider in the diagnosis and/or treatment of cardiac- and cardiopulmonary-related pathologies and medical conditions, or an indicator of one. Examples include significant coronary artery disease (CAD), one or more forms of heart failure such as, e.g., heart failure with preserved ejection fraction (HFpEF), congestive heart failure, various forms of arrhythmia, valve failure, various forms of pulmonary hypertension, hypertrophic cardiomyopathy, among various other disease and conditions disclosed herein.

In addition, there exist possible indicators of a disease or condition, such as an elevated or abnormal left ventricular end-diastolic pressure (LVEDP) value as it relates to some forms of heart failure, abnormal left ventricular ejection fraction (LVEF) values as they relate to some forms of heart failure or an elevated mean pulmonary arterial pressure (mPAP) value as it relates to pulmonary hypertension and/or pulmonary arterial hypertension. Indicators of the likelihood that such indicators are abnormal/elevated or normal, such as those provided by the example analysis and classifiers described herein, can help a healthcare provider assess or diagnose that the patient has or does not have a given disease or condition. In addition to these metrics associated with a disease state of condition, other measurements and factors may be employed by a healthcare professional in making a diagnosis, such as the results of a physical examination and/or other tests, the patient's medical history, current medications, etc. The determination of the presence or non-presence of a disease state or medical condition can include the indication (or a metric of measure that is used in the diagnosis) for such disease.

In FIG. 1, the components include at least one non-invasive biophysical signal recorder or capture system 102 and an assessment system 103 that is located, for example, in a cloud or remote infrastructure or in a local system. Biophysical signal capture system 102 (also referred to as a biophysical signal recorder system), in this embodiment, is configured to, e.g., acquire, process, store and transmit synchronously acquired patient's electrical and hemodynamic signals as one or more types of biophysical signals 104. In the example of FIG. 1, the biophysical signal capture system 102 is configured to synchronously capture two types of biophysical signals shown as first biophysical signals 104a (e.g., synchronously acquired to other first biophysical signals) and second biophysical signals 104b (e.g., synchronously acquired to the other biophysical signals) acquired from measurement probes 106 (e.g., shown as probes 106a and 106b, e.g., comprising hemodynamic sensors for hemodynamic signals 104a, and probes 106c-106h comprising leads for electrical/cardiac signals 104b). In some embodiments, the non-invasive biophysical signal capture system 102 is configured to capture one type of biophysical signals, e.g., first biophysical signals 104a, second biophysical signals 104b, or any of the biophysical signals described herein. In the example shown in FIG. 1, the probes 106a-h are placed on, e.g., by being adhered to or placed next to, a surface tissue of a patient 108 (shown at patient locations 108a and 108b). The patient is preferably a human patient, but it can be any mammalian patient. The acquired raw biophysical signals (e.g., 106a and 106b) together form a biophysical-signal data set 110 (shown in FIG. 1 as a first biophysical-signal data set 110a and a second biophysical-signal data set 110b, respectively) that may be stored, e.g., as a single file, preferably, that is identifiable by a recording/signal captured number and/or by a patient's name and medical record number.

In the FIG. 1 embodiment, the first biophysical-signal data set 110a comprises a set of raw photoplethysmographic, or hemodynamic, signal(s) associated with measured changes in light absorption of oxygenated and/or deoxygenated hemoglobin from the patient at location 108a, and the second biophysical-signal data set 110b comprises a set of raw cardiac or biopotential signal(s) associated with electrical signals of the heart. Though in FIG. 1, raw photoplethysmographic or hemodynamic signal(s) are shown being acquired at a patient's finger, the signals may be alternatively acquired at the patient's toe, wrist, forehead, earlobe, neck, etc. Similarly, although the cardiac or biopotential signal(s) are shown to be acquired via three sets of orthogonal leads, other lead configurations may be used (e.g., 11 lead configuration, 12 lead configuration, etc.).

Plots 110a' and 110b' show examples of the first biophysical-signal data set 110a and the second biophysical-signal data set 110a, respectively. Specifically, Plot 110a' shows an example of an acquired photoplethysmographic or hemodynamic signal. In Plot 110a', the photoplethysmographic signal is a time series signal having a signal voltage potential as a function of time as acquired from two light sources (e.g., infrared and red-light source). Plot 110b' shows an example cardiac signal comprising a 3-channel potential time series plot. In some embodiments, the biophysical signal capture system 102 preferably acquires biophysical signals via non-invasive means or component(s). In alternative embodiments, invasive or minimally-invasively means or component(s) may be used to supplement or as substitutes for the non-invasive means (e.g., implanted pressure sensors, chemical sensors, accelerometers, and the like). In still further alternative embodiments, non-invasive and non-contact probes or sensors capable of collecting biophysical signals may be used to supplement or as substitutes for the non-invasive and/or invasive/minimally invasive means, in any combination (e.g., passive thermometers, scanners, cameras, x-ray, magnetic, or other means of non-contact or contact energy data collection system as discussed herein). Subsequent to signal acquisitions and recording, the biophysical signal capture system 102 then provides, e.g., sending over a wireless or wired communication system and/or a network, the acquired biophysical-signal data set 110 (or a data set derived or processed therefrom, e.g., filtered or pre-processed data) to a data repository 112 (e.g., a cloud-based storage area network) of the assessment system 103. In some embodiments, the acquired biophysical-signal data set 110 is sent directly to the assessment system 103 for analysis or is uploaded to a data repository 112 through a secure clinician's portal.

Biophysical signal capture system 102 is configured with circuitries and computing hardware, software, firmware, middleware, etc., in some embodiments, to acquire, store, transmit, and optionally process both the captured biophysical signals to generate the biophysical-signal data set 110. An example biophysical signal capture system 102 and the acquired biophysical-signal set data 110 are described in U.S. Pat. No. 10,542,898, entitled "Method and Apparatus for Wide-Band Phase Gradient Signal Acquisition," or U.S. Patent Publication No. 2018/0249960, entitled "Method and Apparatus for Wide-Band Phase Gradient Signal Acquisition," each of which is hereby incorporated by reference herein in its entirety.

In some embodiments, biophysical signal capture system 102 includes two or more signal acquisition components, including a first signal acquisition component (not shown) to acquire the first biophysical signals (e.g., photoplethysmographic signals) and includes a second signal acquisition component (not shown) to acquire the second biophysical signals (e.g., cardiac signals). In some embodiments, the electrical signals are acquired at a multi-kilohertz rate for a few minutes, e.g., between 1 kHz and 10 kHz. In other embodiments, the electrical signals are acquired between 10 kHz and 100 kHz. The hemodynamic signals may be acquired, e.g., between 100 Hz and 1 kHz.

Biophysical signal capture system 102 may include one or more other signal acquisition components (e.g., sensors such as mechano-acoustic, ballistographic, ballistocardiographic, etc.) for acquiring signals. In other embodiments of the signal capture system 102, a signal acquisition component comprises conventional electrocardiogram (ECG/EKG) equipment (e.g., Holter device, 12 lead ECG, etc.).

Figure 13A:
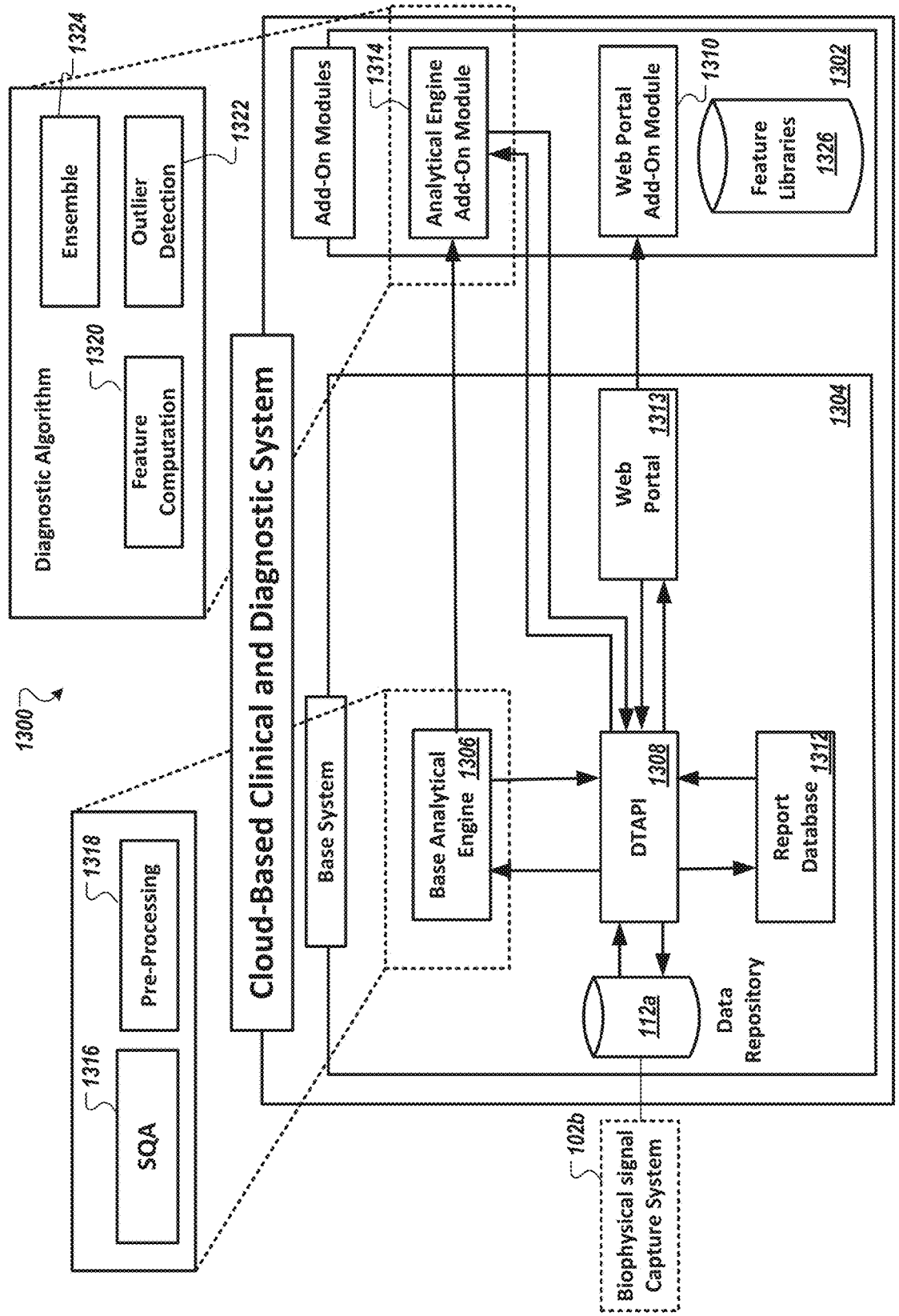
FIG. 13A shows a schematic diagram of an example clinical evaluation system configured to use the cycle variability-related features among other computed features to generate one or more metrics associated with the physiological state of a patient in accordance with an illustrative embodiment.
Figure 13B:
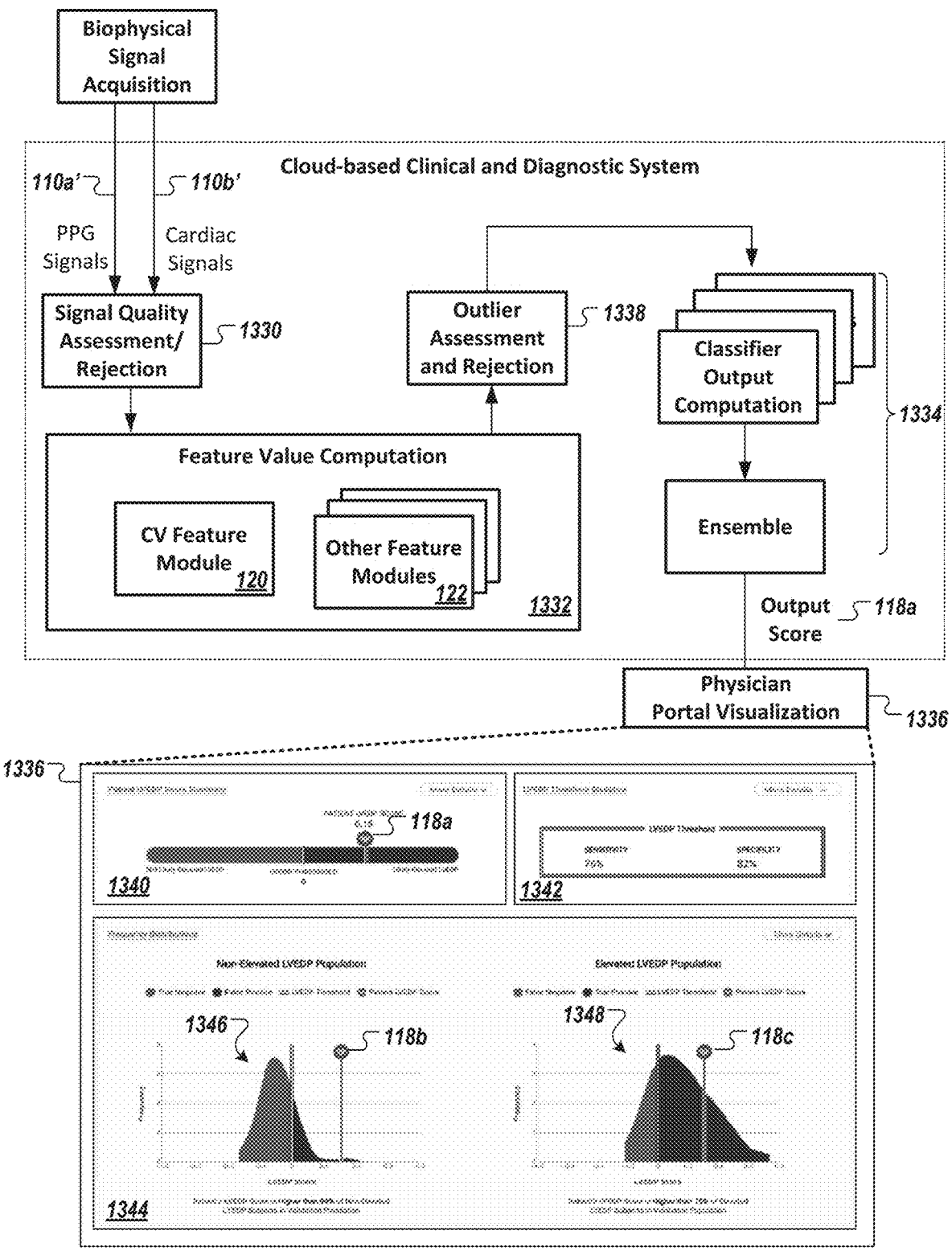
FIG. 13B shows a schematic diagram of the operation of the example clinical evaluation system of FIG. 13A in accordance with an illustrative embodiment.

Assessment system 103 comprises, in some embodiments, the data repository 112 and an analytical engine or analyzer (not shown—see FIGS. 13A and 13B). Assessment system 103 may include feature modules 114 and a classifier module 116 (e.g., an ML classifier module). In FIG. 1, Assessment system 103 is configured to retrieve the acquired biophysical signal data set 110, e.g., from the data repository 112, and use it in the feature modules 114, which is shown in FIG. 1 to include a cycle variability-associated feature module 120 and other modules 122 (later described herein). The features modules 114 compute values of features or parameters, including those of cycle variability-related features to provide to the classifier module 116, which computes an output 118, e.g., an output score, of the metrics associated with the physiological state of a patient (e.g., an indication of the presence or non-presence of a disease state, medical condition, or an indication of either). Output 118 is subsequently presented, in some embodiments, at a healthcare physician portal (not shown—see FIGS. 13A and 13B) to be used by healthcare professionals for the diagnosis and treatment of pathology or a medical condition. In some embodiments, a portal may be configured (e.g., tailored) for access by, e.g., patient, caregivers, researchers, etc., with output 118 configured for the portal's intended audience. Other data and information may also be a part of output 118 (e.g., the acquired biophysical signals or other patient's information and medical history).

Classifier module 116 (e.g., ML classifier module) may include transfer functions, loop up tables, models, or operators developed based on algorithms such as but not limited to decision trees, random forests, neural networks, linear models, Gaussian processes, nearest neighbor, SVMs, Naïve Bayes, etc. In some embodiments, classifier module 116 may include models that are developed based on ML techniques described in concurrently filed U.S. provisional patent application entitled "Method and System to Non-Invasively Assess Elevated Left Ventricular End-Diastolic Pressure"; U.S. Patent Publication No. 20190026430, entitled "Discovering Novel Features to Use in Machine Learning Techniques, such as Machine Learning Techniques for Diagnosing Medical Conditions"; or U.S. Patent Publication No. 20190026431, entitled "Discovering Genomes to Use in Machine Learning Techniques," each of which is hereby incorporated by reference herein in its entirety.

Example Biophysical Signal Acquisition.

Figure 2:
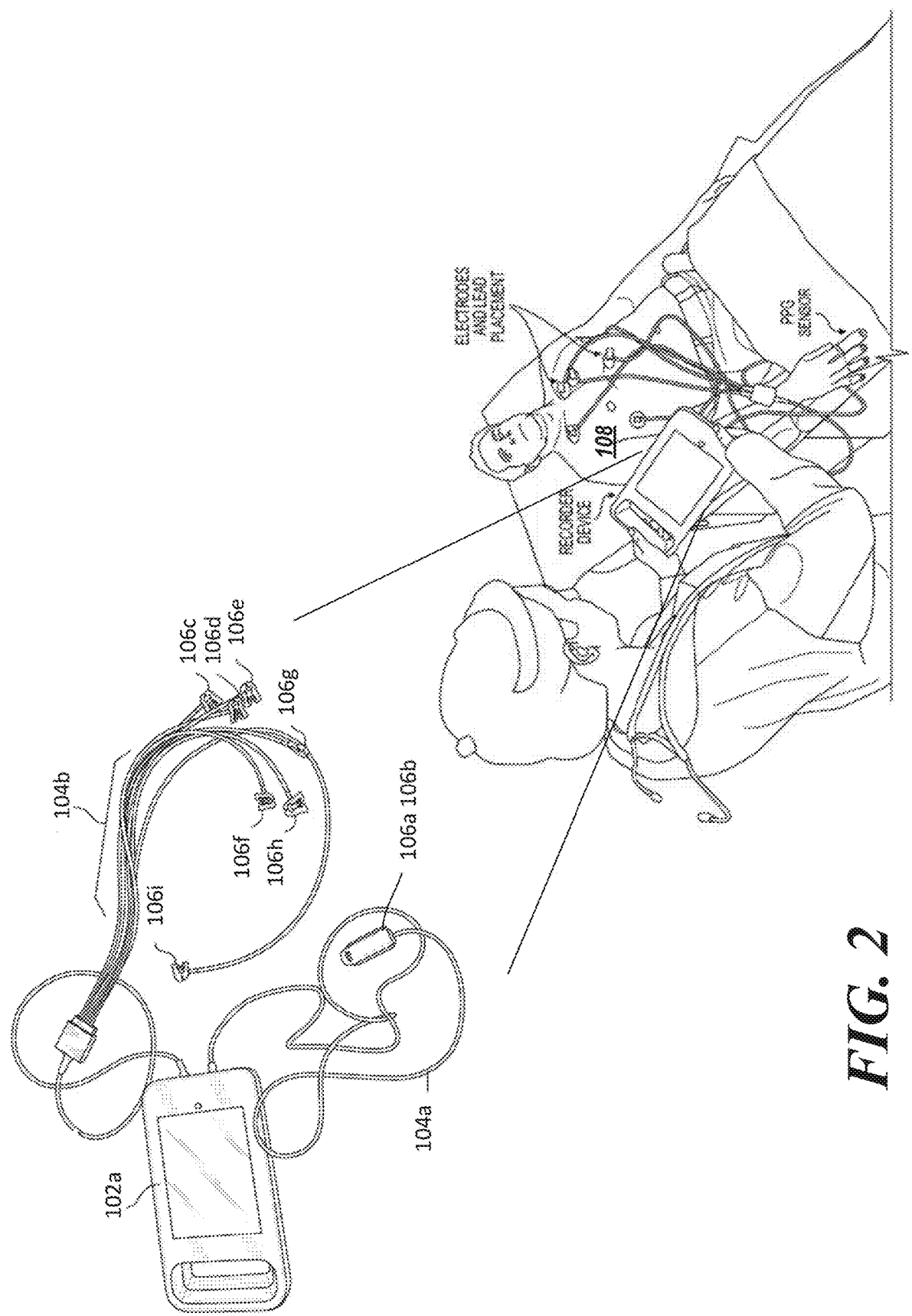
FIG. 2 shows an example biophysical signal capture system or component and its use in non-invasively collecting biophysical signals of a patient in a clinical setting in accordance with an illustrative embodiment.

FIG. 2 shows a biophysical signal capture system 102 (shown as 102a) and its use in non-invasively collecting biophysical signals of a patient in a clinical setting in accordance with an illustrative embodiment. In FIG. 2, the biophysical signal capture system 102a is configured to capture two types of biophysical signals from the patient 108 while the patient is at rest. The biophysical signal capture system 102a synchronously acquires the patient's (i) electrical signals (e.g., cardiac signals corresponding to the second biophysical-signal data set 110b) from the torso using orthogonally placed sensors (106c-106h; 106i is a $7^{th}$ common-mode reference lead) and (ii) hemodynamic signals (e.g., PPG signals corresponding to the first biophysical-signal data set 110a) from the finger using a photoplethysmographic sensor (e.g., collecting signals 106a, 106b).

As shown in FIG. 2, the electrical and hemodynamic signals (e.g., 104a, 104b) are passively collected via commercially available sensors applied to the patient's skin. The signals may be acquired beneficially without patient exposure to ionizing radiation or radiological contrast agents and without patient exercise or the use of pharmacologic stressors. The biophysical signal capture system 102a can be used in any setting conducive for a healthcare professional, such as a technician or nurse, to acquire the requisite data and where a cellular signal or Wi-Fi connection can be established.

The electrical signals (e.g., corresponding to the second biophysical signal data set 110b) are collected using three orthogonally paired surface electrodes arranged across the patient's chest and back along with a reference lead. The electrical signals are acquired, in some embodiments, using a low-pass anti-aliasing filter (e.g., ~2 kHz) at a multi-kilohertz rate (e.g., 8 thousand samples per second for each of the six channels) for a few minutes (e.g., 215 seconds). In alternative embodiments, the biophysical signals may be continuously/intermittently acquired for monitoring, and portions of the acquired signals are used for analysis. The hemodynamic signals (e.g., corresponding to the first biophysical signal data set 110a) are collected using a photoplethysmographic sensor placed on a finger. The photoabsorption of red light (e.g., any wavelengths between 600-750 nm) and infrared light (e.g., any wavelengths between 850-950 nm) are recorded, in some embodiments, at a rate of 500 samples per second over the same period. The biophysical signal capture system 102a may include a common mode drive that reduces common-mode environmental noise in the signal. The photoplethysmographic and cardiac signals were simultaneously acquired for each patient. Jitter (inter-modality jitter) in the data may be less than about 10 microseconds (μs). Jitter among the cardiac signal channels may be less than 10 microseconds, e.g., around ten femtoseconds (fs).

A signal data package containing the patient metadata and signal data may be compiled at the completion of the signal acquisition procedure. This data package may be encrypted before the biophysical signal capture system 102a transferring to the data repository 112. In some embodiments, the data package is transferred to the assessment system (e.g., 103). The transfer is initiated, in some embodiments, following the completion of the signal acquisition procedure without any user intervention. The data repository 112 is hosted, in some embodiments, on a cloud storage service that can provide secure, redundant, cloud-based storage for the patient's data packages, e.g., Amazon Simple Storage Service (i.e., "Amazon S3"). The biophysical signal capture system 102a also provides an interface for the practitioner to receive notification of an improper signal acquisition to alert the practitioner to immediately acquire additional data from the patient.

Example Method of Operation

Figure 3A:
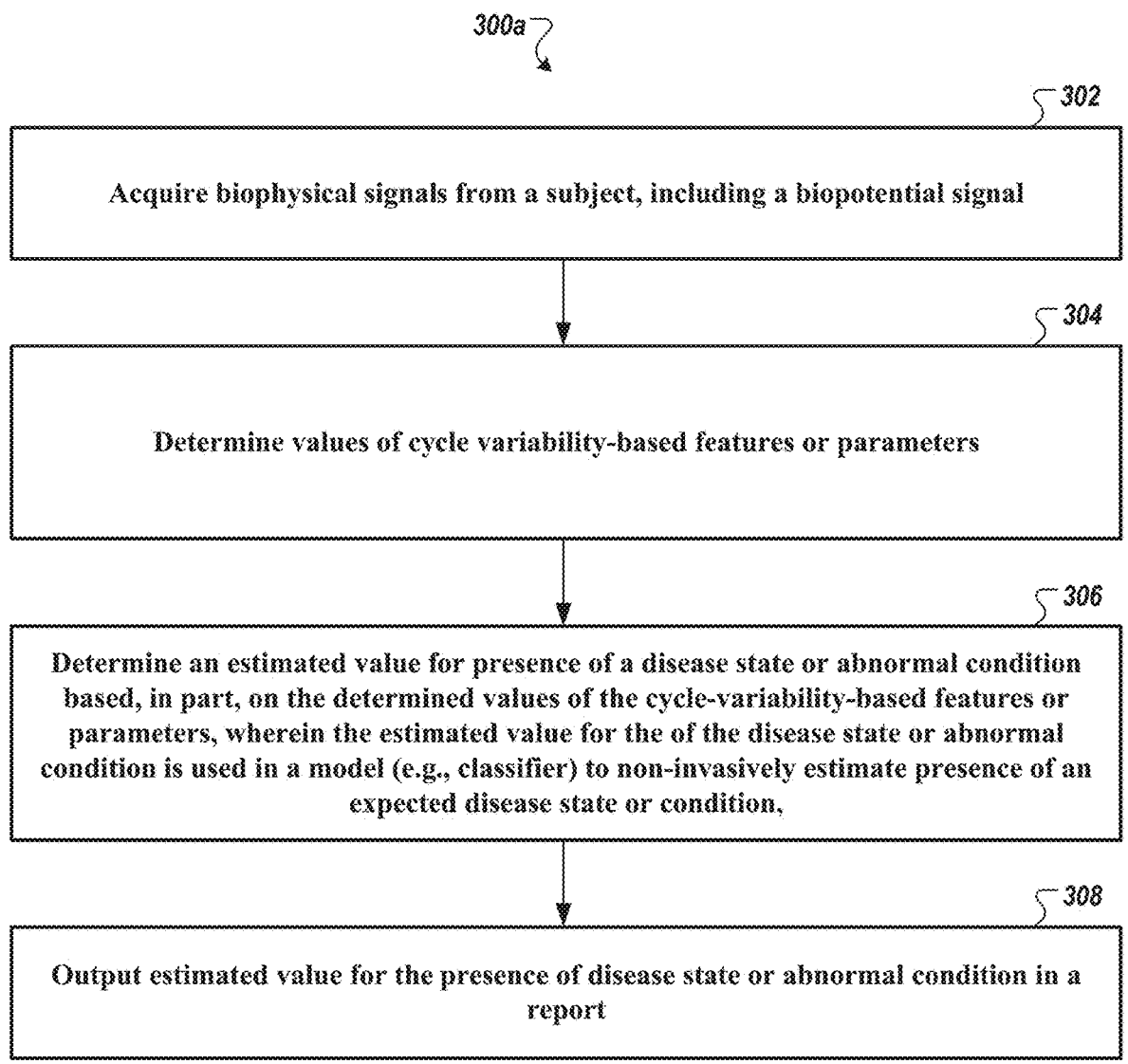
FIGS. 3A and 3B each shows an example method to use cycle variability-related features/parameters or their intermediate data in a practical application for diagnostics, treatment, monitoring, or tracking.
Figure 3B:
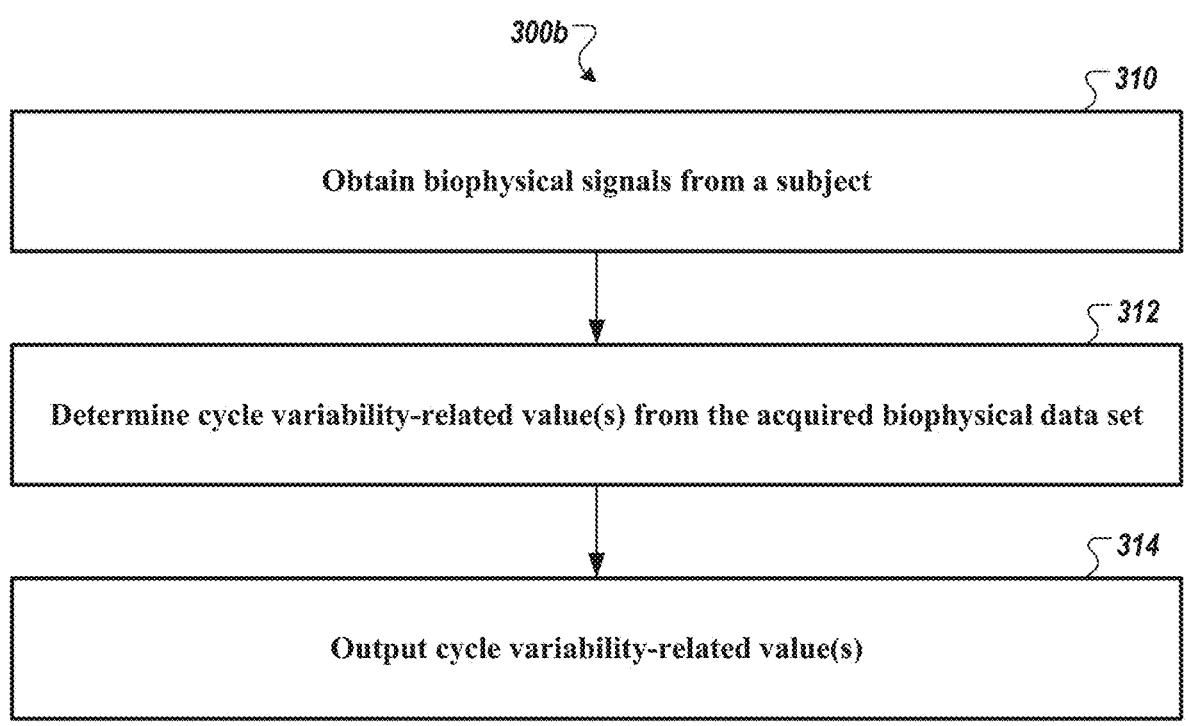

FIGS. 3A-3B each shows an example method to use cycle variability-related features or their intermediate outputs in a practical application for diagnostics, treatment, monitoring, or tracking.

Estimation of Presence of Disease State or Indicating Condition. FIG. 3A shows a method 300a that employs cycle variability-related parameters or features to determine estimators of the presence of a disease state, medical condition, or indication of either, e.g., to aid in the diagnosis, tracking, or treatment. Method 300a includes the step of acquiring (302) biophysical signals from a patient (e.g., cardiac signals, photoplethysmographic signals, ballistocardiographic signals), e.g., as described in relation to FIGS. 1 and 2 and other examples as described herein. In some embodiments, the acquired biophysical signals are transmitted for remote storage and analysis. In other embodiments, the acquired biophysical signals are stored and analyzed locally.

As stated above, one example in the cardiac context is the estimation of the presence of abnormal left-ventricular end-diastolic pressure (LVEDP) or mean pulmonary artery pressure (mPAP), significant coronary artery disease (CAD), abnormal left ventricular ejection fraction (LVEF), and one or more forms of pulmonary hypertension (PH), such as pulmonary arterial hypertension (PAH). Other pathologies or indicating conditions that may be estimated include, e.g., one or more forms of heart failure such as, e.g., heart failure with preserved ejection fraction (HFpEF), arrhythmia, congestive heart failure, valve failure, hypertrophic cardiomyopathy, among various other disease and medical conditions disclosed herein.

Method 300a further includes the step of retrieving (304) the data set and determining values of cycle variability-related features that describe the spectral or information content that is in-band to the frequency range of the signal and has a similar amplitude but is not synchronized with the cardiac cycle. Example operations to determine the values of cycle variability-related features are provided in relation to FIGS. 4-12 later discussed herein. Method 300a further includes the step of determining (306) an estimated value for a presence of a disease state, medical condition, or an indication of either based on an application of the determined cycle variability-related features to an estimation model (e.g., ML models). An example implementation is provided in relation to FIGS. 13A and 13B.

Method 300a further includes the step of outputting (308) estimated value(s) for the presence of disease state or abnormal condition in a report (e.g., to be used diagnosis or treatment of the disease state, medical condition, or indication of either), e.g., as described in relation to FIGS. 1, 13A, and 13B and other examples described herein.

Diagnostics or Condition Monitoring or Tracking using Cycle Variability Features. FIG. 3B shows a method 300b that employs cycle-variability-related parameters or features for the monitoring health or controls of medical equipment or health monitoring device. Method 300b includes the step of obtaining (302) biophysical signals from a patient (e.g., cardiac signals, photoplethysmographic signals, ballistocardiographic signals, etc.). The operation may be performed continuously or intermittently, e.g., to provide output for a report or as controls for the medical equipment or the health monitoring device.

Method 300b further includes determining (310) cycle-variability-related value(s) from the acquired biophysical data set, e.g., as described in relation to FIGS. 4-12.

Method 300b further includes outputting (312) the cycle-variability-related value(s) (e.g., in a report for use in diagnostics or as signals for controls). For monitoring and tracking, the output may be via a wearable device, a hand-held device, or medical diagnostic equipment (e.g., pulse oximeter system, wearable health monitoring systems) to provide augmented data associated with health. In some embodiments, the outputs may be used in resuscitation systems, cardiac or pulmonary stress test equipment, pacemakers, etc.

Cycle Variability Features or Parameters

Figure 4:
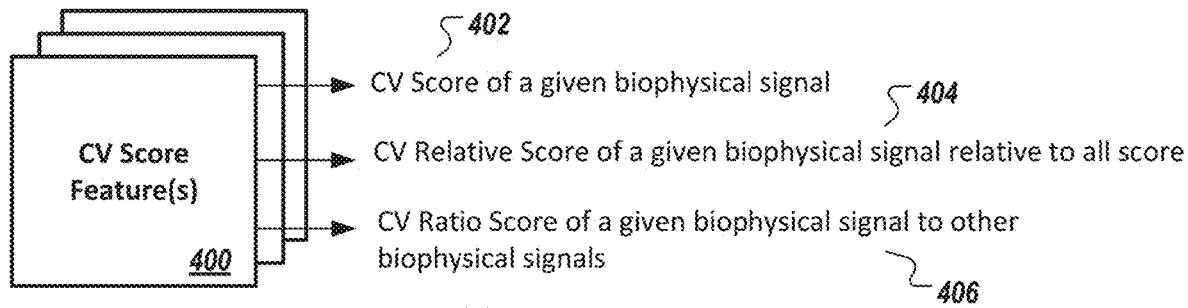
FIG. 4 illustrates an example cycle variability score analysis feature computation module configured to determine values of cycle-variability associated properties of an acquired biophysical signal in accordance with an illustrative embodiment.
Figure 5:
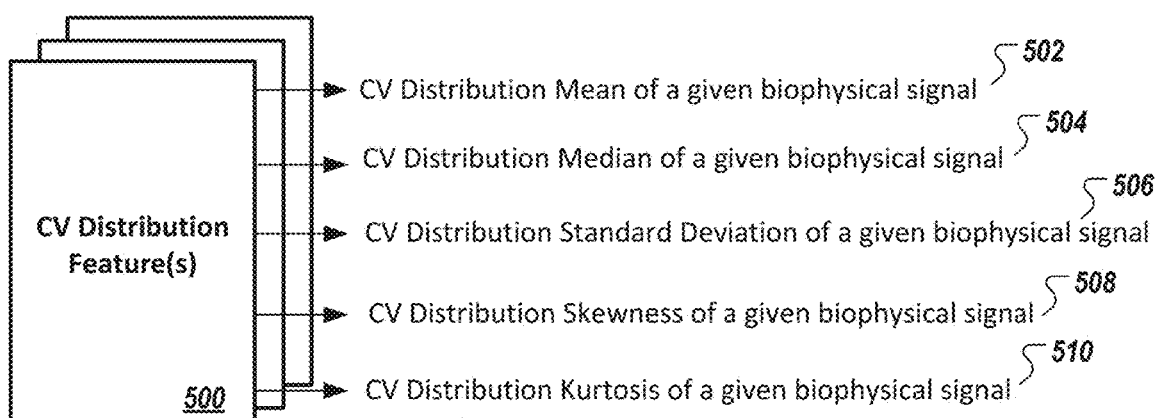
FIG. 5 illustrates an example cycle variability distribution analysis feature computation module configured to determine values of cycle-variability distribution properties of an acquired biophysical signal in accordance with an illustrative embodiment.
Figure 6:
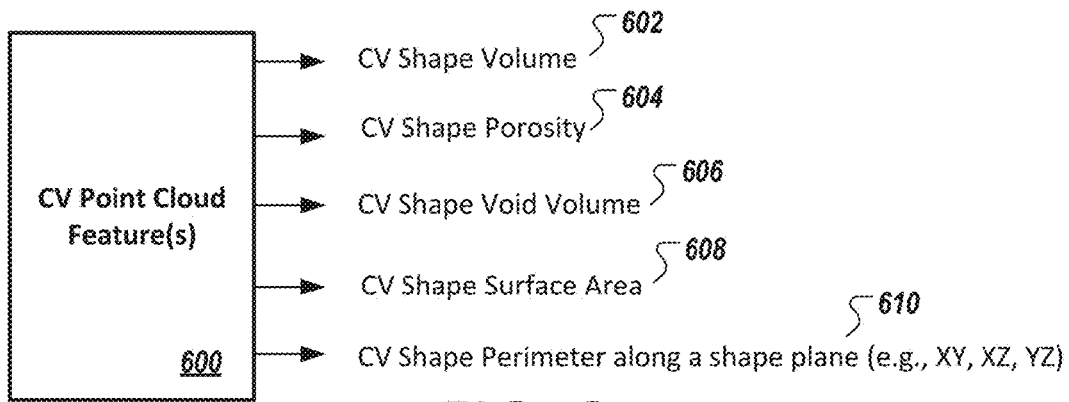
FIG. 6 illustrates an example cycle-variability point-cloud analysis feature computation module configured to determine values of geometric parameters of a three-dimensional phase space model (e.g., an alpha shape model) of the calculated CV residue in accordance with an illustrative embodiment.
Figure 7A:
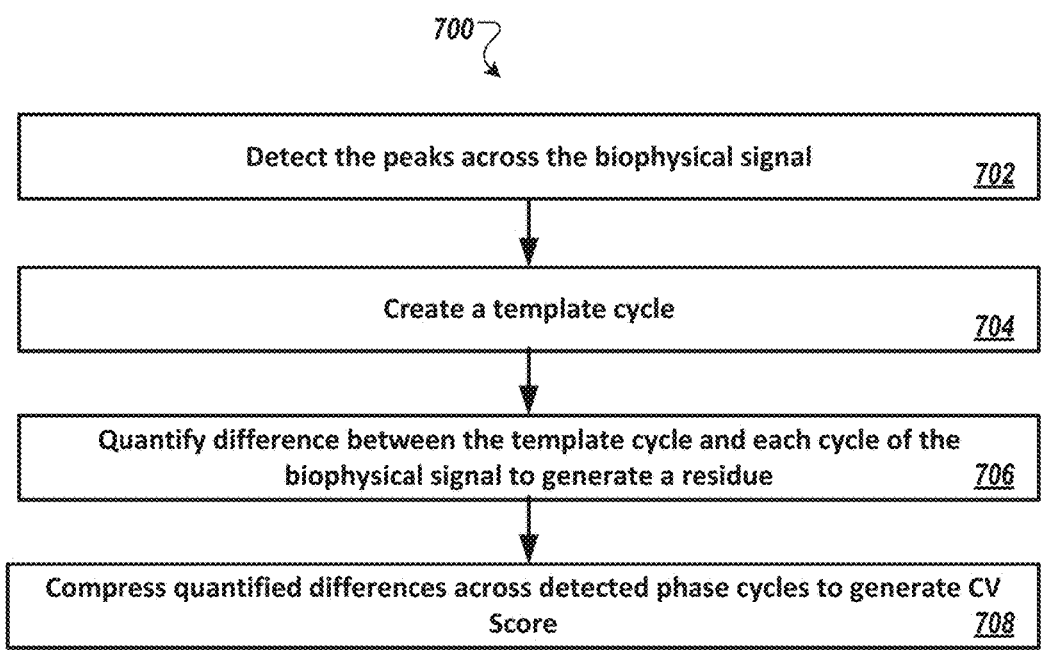
FIG. 7A is a diagram of an exemplary method to generate cycle-variability score features for the computation module of FIG. 4 in accordance with an illustrative embodiment.
Figure 7B:
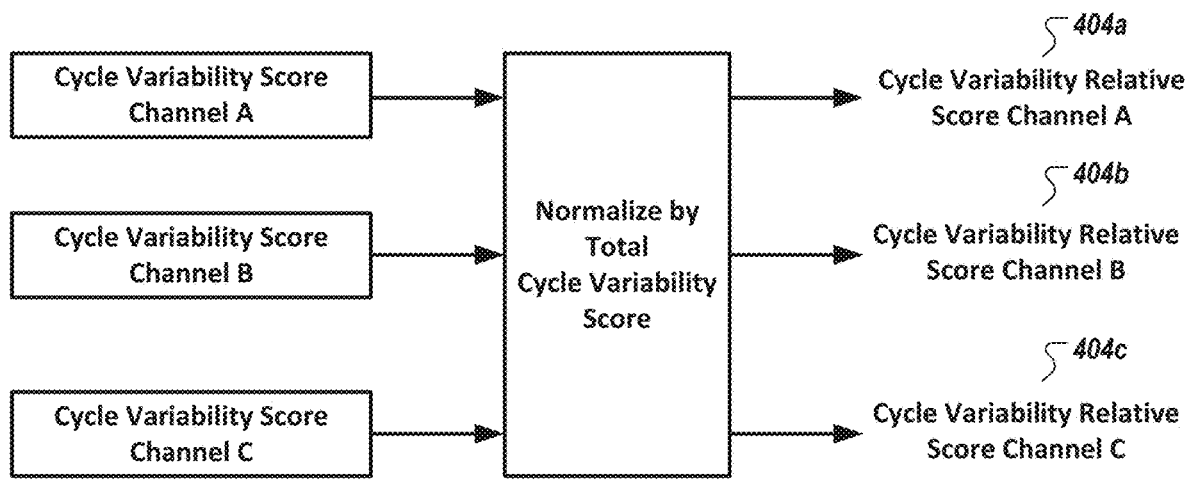
FIG. 7B shows a diagram to generate cycle-variability relative scores in accordance with an illustrative embodiment.
Figure 7C:
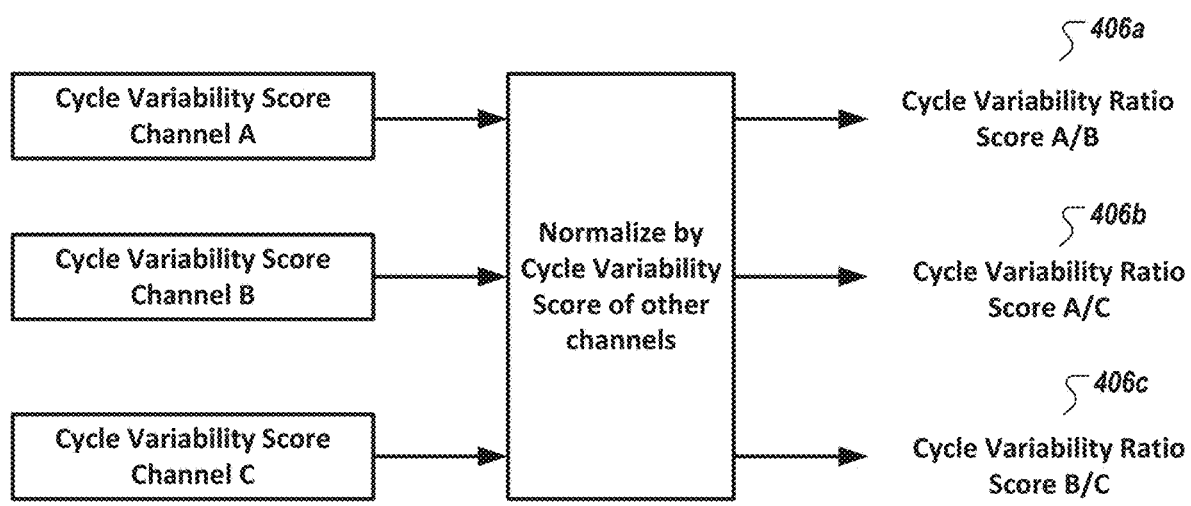
FIG. 7C shows a diagram of an exemplary method to generate cycle-variability ratio scores in accordance with an illustrative embodiment.

FIGS. 4, 5, and 6 each shows an example cycle variability analysis feature computation module, for a total of three example modules configured to determine values of cycle variability features or parameters of biophysical signals in accordance with an illustrative embodiment. The cycle variability score analysis feature computation module 400 can calculate a score-based metric for cycle variability (shown in FIG. 4, including CV score, CV relative score, and CV ratio score). The cycle variability distribution analysis feature computation module 500 can calculate the distribution of the values of cycle variability and provide a statistical assessment as the feature output of that distribution. The cycle-variability point-cloud analysis feature computation module 600 can generate a point cloud from the cycle variability data to which an encapsulated volumetric object can be generated and various topological and morphological characteristics of the volumetric object can be determined, such as volume, porosity, surface, perimeters. FIGS. 7A, 7B, and 7C, respectively, show example operations of the cycle variability analysis feature computation module of FIGS. 4, 5, and 6.

Example #1—Cycle Variability Score Features

FIG. 4 illustrates, as a first of three example feature or parameter categories, an example of the cycle variability score analysis feature computation module 400 (shown as "CV Score Feature(s)" 400) configured to determine values of the cycle-variability associated score of one or more acquired biophysical signals in accordance with an illustrative embodiment. In the example shown in FIG. 4, Module 400 is configured to output a cycle-variability score 402 a given signal. For a cardiac cycle, e.g., with 3 channels, a cycle-variability score may be generated for each of the three channels. Module 400 may also generate a cycle-variability relative score 404 that normalizes (e.g., dynamic scaling, mean max, z-transform, etc.) each cycle-variability score for a given channel to all the calculated score (e.g., for all three channels). In other embodiments non-normalize values can be used for the score calculation. Module 400 may also generate a cycle-variability ratio score 406 that determines a ratio between the cycle-variability score for a given channel to the cycle-variability score for another channel.

Table 2 shows an example set of 9 extractable cycle-variability features and their corresponding description. In Table 2, features (shown with "*") have been observed to have significant utility in the assessment of the presence or non-presence of at least one cardiac disease or condition—specifically, the determination of presence or non-presence of elevated LVEDP. The list of the specific features determined to have significant utility in the assessment of the presence or non-presence of abnormal or elevated LVEDP is provided in Table 7.

TABLE 2

| | Feature name | Description |
|---|---|---|
| 1 | CV_score X* | Cycle variability score of channel X of cardiac signals ($CV_x$) |
| 2 | CV_score Y | Cycle variability score of channel Y of cardiac signals ($CV_y$) |

TABLE 2-continued

| Feature name | Description | |
|---|---|---|
| 3 | CV_score Z | Cycle variability score of channel Z of cardiac signals(CV$_z$) |
| 4 | CV_relative_X | $\dfrac{CV_x}{CV_x + CV_y + CV_z}$ |
| 5 | CV_relative_Y | $\dfrac{CV_y}{CV_x + CV_y + CV_z}$ |
| 6 | CV_relative_Z | $\dfrac{CV_z}{CV_x + CV_y + CV_z}$ |
| 7 | CV_ratio_XY | $\dfrac{CV_x}{CV_y}$ |
| 8 | CV_ratio_XZ | $\dfrac{CV_x}{CV_z}$ |
| 9 | CV_ratio_YZ | $\dfrac{CV_y}{CV_z}$ |

Cycle Variability Score Computation. FIG. 7A is a diagram of an exemplary method 700 to generate a cycle-variability score (e.g., "CV_score X" $CV_x$ "CV_score Y" $CV_y$, "CV_score Z" $CV_z$) of a biophysical signal in accordance with an illustrative embodiment. Method 700 includes detecting peaks (702) in all, or a substantial portion, of the biophysical signal for a quasi-periodic cycle. For cardiac signals, the peaks may be points of ventricular depolarization (also commonly referred to as "R-peaks"), which are a point in the signal during each cycle when the electrical activation of the ventricles is maximal. In some embodiments, Method 700 employs a Pan-Tompkins algorithm for ventricular depolarization detection, for example, as described in Pan & Tompkins, A Real Time QRS Detection Algorithm, IEEE Transactions on Biomedical Engineering, Volume 32-3, 230-236, 1985, the entirety of which is hereby incorporated by reference herein in its entirety. Other algorithms may be used to detect peaks in the cardiac signal data set—examples include those described in Makwana et al. "Hilbert transform based adaptive ECG R-peak detection technique," International Journal of Electrical and Computer Engineering, 2(5), 639 (2012); Lee et al., "Smart ECG Monitoring Patch with Built-in R-Peak Detection for Long-Term HRV Analysis," Annals of Biomedical Engineering. 44(7), 2292-3201 (2016); and Kim et al., "Detection of R-Peaks in ECG Signal by Adaptive Linear Neuron (ADALINE)," Artificial Neural Network, presented at MATEC Web of Conferences, 54, 10001 (2016), each of which is hereby incorporated by reference herein in its entirety. Various PPG peak detectors may be used for photoplethysmographic signals.

Method 700 then includes determining or creating (704) a template-signal vector data set (also referred to as a template cycle). The template-signal vector data set represents a quasi-periodic signal pattern of the subject (e.g., a heart-beat pattern for cardiac signals). The term "quasi-periodic" can also be referred to in more general terms as a characteristic of a signal system that cycles with, at a minimum, two frequency components, of which the ratio is not a rational number. In some embodiments, to determine the template-signal vector data set, a median peak-peak interval (e.g., R-R intervals for cardiac signals) is calculated using the detected peak locations. The cycle region is set around each peak and normalized for the amplitude. The cycle region includes regions of interest, for example, the P and completion of the T wave for cardiac signals.

Figure 8A:
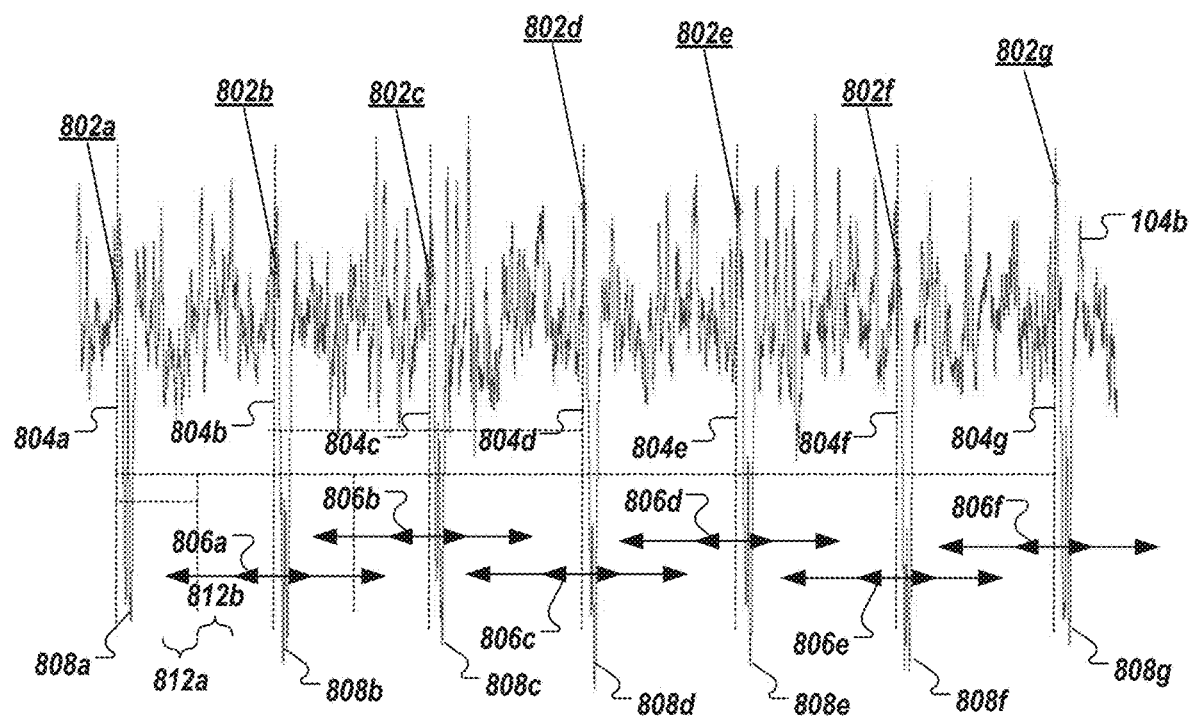
FIG. 8A shows a plot illustrating the method of generating a template-signal vector data set employed by the feature computation modules of FIGS. 4-6 in accordance with an illustrative embodiment.

In FIG. 8A, the detected peak locations of cardiac signal 104b (e.g., shown as 802a-802g) are used to determine a median peak-to-peak interval (e.g., median R-R peaks for portions of the cardiac signal 104b as shown with 804a-804g) and to set a cycle region (e.g., shown as 806a-806f) around each peak (e.g., R-peaks for portions of cardiac signals 104b as shown with 808a-808g). FIG. 8A further shows that the cycle region is set around the R-peak and includes both the P wave and the completion of the T wave for cardiac signal 104b. In FIG. 8A, the ranges are from about −20% to about +20% of the median interval (e.g., shown as 812a, 812b). Each of the cycle regions (e.g., 806a-806f) can be stored by a processor in a matrix (also referred to as a "cycle matrix"). The cycle matrix may have the size M×N in which M is the number of detected cycles, and N is 40% (or other range) of the median peak-to-peak interval (e.g., median R-R intervals for cardiac signals) in which the 40% of the peak-to-peak interval represents the full temporal "width" of the cycle. Specifically, once the median peak-to-peak interval (e.g., median R-R interval for cardiac signals) is known across the dataset, the signal can be divided in half, e.g., to get the "20%" that reaches both forward and backward in time from the peak (e.g., R-peak) to capture the other waves (e.g., T wave and P wave for a cardiac signal). Of course, other cycle region lengths can be used for cardiac signals and for the various distinct waves in brain signals, etc. For example, ranges that may be applied include, but are not limited to, from −10% to 10%, −15% to 15%, −25% to 25%. In addition, rather than a median of the peak-to-peak interval, the mean of the peak-to-peak interval may also be used.

Figure 8B:
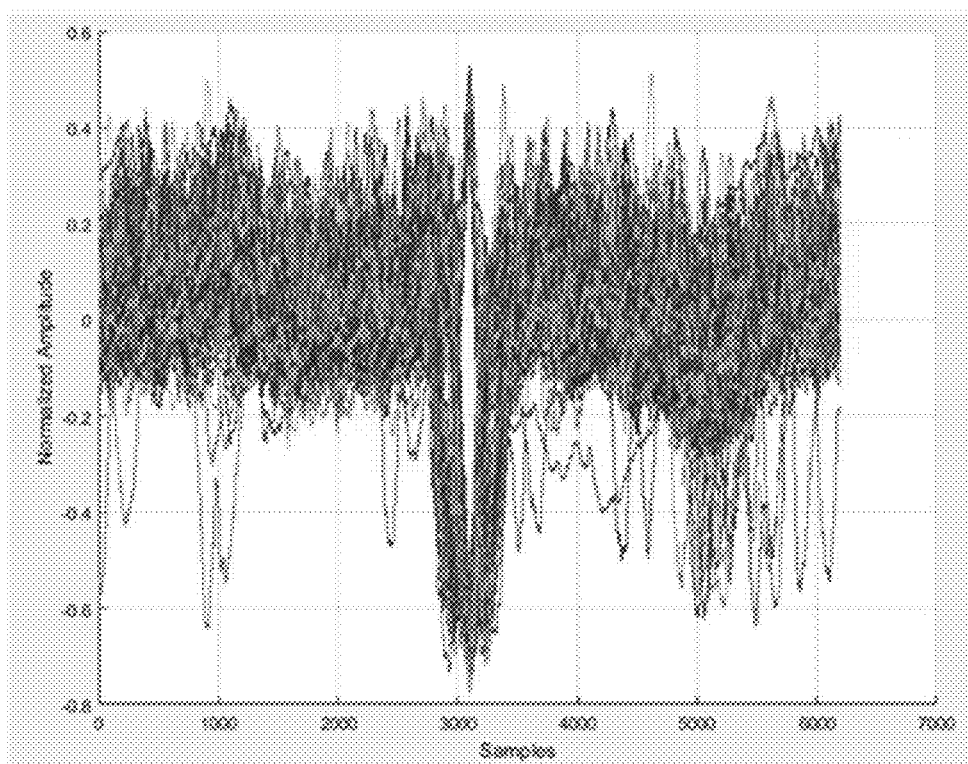
FIG. 8B shows a plot of multiple cycles the signals of the template-signal vector data set across presented within a window in accordance with an illustrative embodiment.

FIG. 8B shows a plot of results of the normalization process in accordance with an illustrative embodiment. In FIG. 8B, each cycle region (e.g., shown as 806a-806f in FIG. 8A) of the biophysical-signal data set (e.g., cardiac signal data set 110b) is normalized by a processor to remove any offsets such that the average value of each cycle region is zero. The normalized cardiac signal data set, as shown, can have a range of "1" and "−1," though that range can vary depending on the distribution of the data. The normalization process can be employed in embodiment when calculating for the cycle variability feature. In other embodiments, non-normalized signals may be used. In addition to mean and scaling normalization, other normalization methods may be employed. Examples of other normalization methods include Z-transform and mean Max, among others.

Figure 9A:
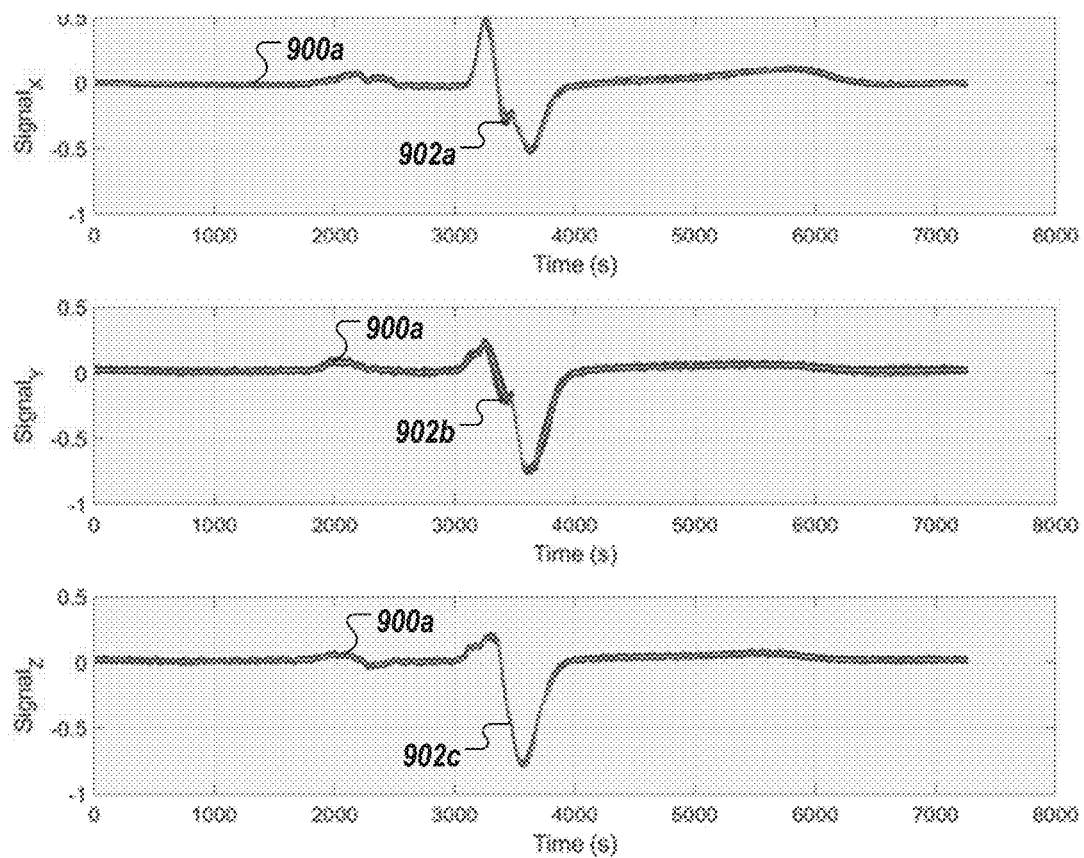
FIG. 9A shows three plots of the determined template-signal vector data in reference to a respective biophysical signal in accordance with an illustrative embodiment.
Figure 9B:
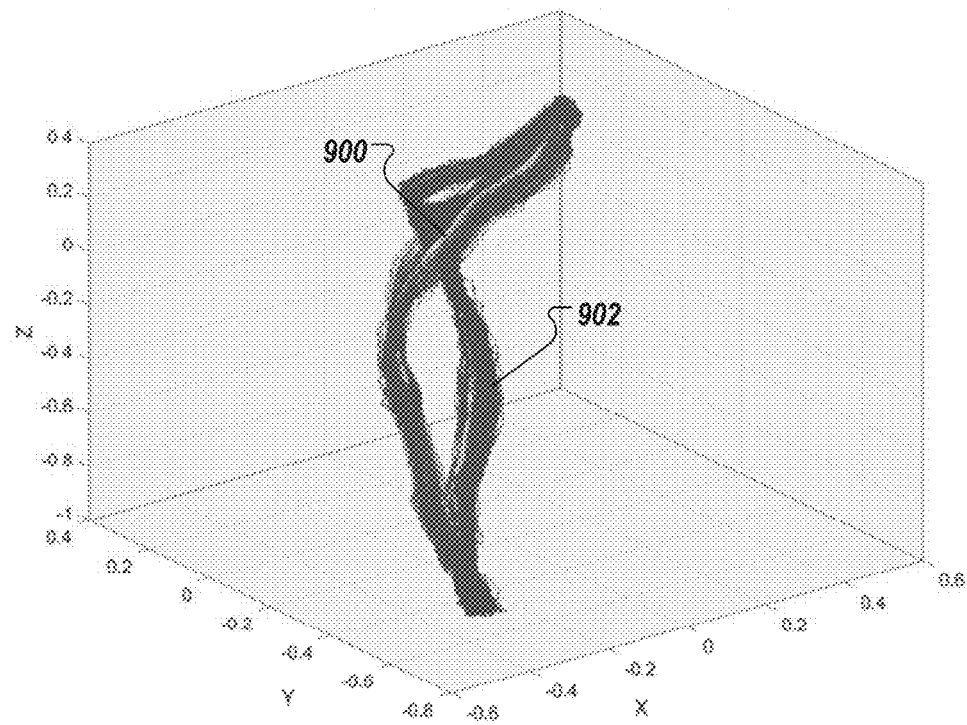
FIG. 9B shows the determined template-signal vector data set of FIG. 9A in phase space in accordance with an illustrative embodiment.

FIG. 9A shows three plots of determined template-signal vector data 900 (shown as 900a, 900b, and 900c) in reference to one of the cycles 902 (shown as 902a, 902b, and 902c). In FIG. 9A, the template-signal vector data set is shown for each of the three cardiac signals. In some embodiments, the same template-signal vector data set calculated for one representative cycle is used to assess against all of the cycles of that given signal. FIG. 9B shows in phase space the determined template-signal vector data set 900 of FIG. 9A across the multiple cycles. In the phase space plot of FIG. 9B, each value of the template-signal vector data set corresponding to the same time instance is shown in the three-dimensional space. The values for all the channels of the acquired biophysical signals are also concurrently displayed in the X, Y, and Z-axis.

Figure 9C:
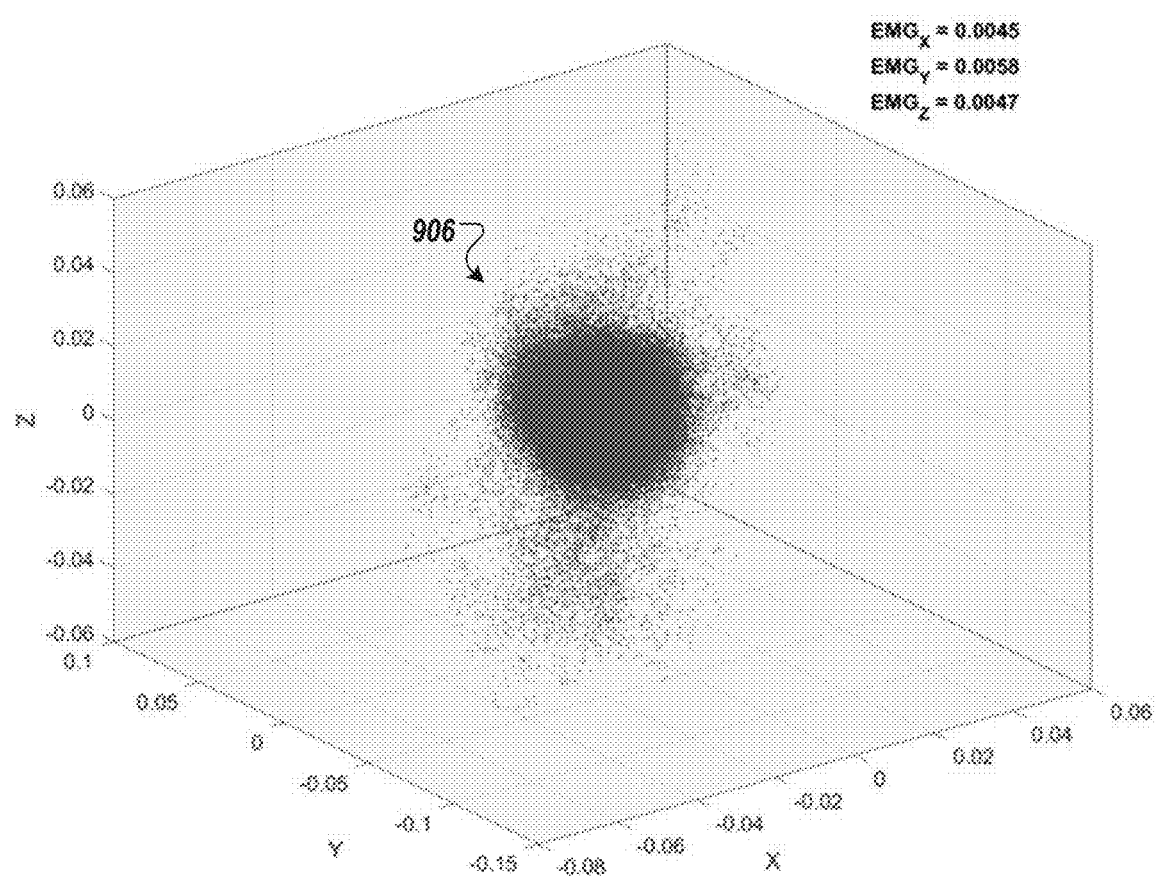
FIG. 9C shows a phase space plot of the residue calculated between the corresponding biophysical cycle and template-signal vector data in accordance with an illustrative embodiment.

Referring back to FIG. 7A, Method 700 then includes quantifying (706) the difference between each detected biophysical cycle and the template-signal vector data set. In some embodiments, the template-signal vector data set is subtracted from each of the detected biophysical cycles to generate a residue data set. FIG. 9C shows a plot of the residue 906 calculated between the detected biophysical cycle and the template-signal vector data set in phase space. Each axis in FIG. 9C represents a channel (channels X, Y, and Z) of the acquired signals. As discussed herein, the residue can be determined from normalized data or non-normalized data using mean and scaling normalization, z-transforms, mean Max, among others.

Referring to FIG. 7A, Method 700 then includes combining the resultant differences across the detected phase cycles to create the final cycle variability score (CVS) for the channel. The cycle variability score, in some embodiments, is a median of the calculated residue data set for each given signal (e.g., 1 score per channel). In other embodiments, the cycle variability score is a median of the calculated residue data set for all of the signals (e.g., 1 score per set of channels). In some embodiments, the cycle variability score is calculated from a subset of the acquired signals. In another embodiment, the cycle variability score is a mean of the calculated residue data set for a given signal. In yet another embodiment, the cycle variability score is a mean of the calculated residue data set for all of the signals, or a representative subset of such signals.

In some embodiments, the cycle variability score is a Z-score value for a given data point in the template signal vector data set and is calculated as a difference between the value of the given data point and a mean of a set of cycles in which the difference is then normalized by the standard deviation of that given data point to the same indexed data value of the set of cycles.

Cycle Variability Relative Score Computation. FIG. 7B shows a diagram of a method to generate cycle-variability relative scores 404 (shown as 404a, 404b, 404c) that normalize each cycle-variability score for a given channel to all the calculated score (e.g., for all three channels). In FIG. 7B, the cycle-variability relative scores 404a, 404b, 404c are shown for three channels. The cycle-variability relative score 404a, 404b, 404c for a channel n may be calculated over the sum of all the calculated scores, as shown in Equation 1:

$$\frac{CV_n}{\sum_1^n CV_n} \quad \text{(Equation 1)}$$

In Table 2, the cycle-variability relative scores 404 are shown as "CV_relative_X," "CV_relative_Y," and "CV_relative_Z."

Cycle Variability Ratio Computation. FIG. 7C shows a diagram to generate cycle-variability ratio scores 406 (shown as 406a, 406b, and 406c) that normalize each cycle-variability score as a ratio between two channels. In FIG. 7C, the cycle-variability ratio scores 406a, 406b, 406c are shown for three channels. In Table 2, the cycle-variability ratio scores 406a, 406b, and 406c are shown as "CV_ratio_XY," "CV_ratio_XZ," and "CV_ratio_YZ," respectively.

Example #2—Cycle Variability Statistical Distribution Feature

FIG. 5 illustrates, as a second of three example feature or parameter categories, an example cycle variability distribution analysis feature computation module 500 (shown as "CV Distribution Feature(s)" 500) configured to determine an assessment comprising statistical parameters of the distribution of calculated cycle-variability values for the acquired biophysical signals in accordance with an illustrative embodiment. In the example shown in FIG. 5, the statistical assessment can include a mean (502), median (504), standard deviation (506), skewness (508), and kurtosis (510) of an assessed distribution.

Table 3 lists an example set of cycle-variability features and their corresponding description. In Table 3, features (shown with "*") have been observed to have significant utility in the assessment of the presence or non-presence of at least one cardiac disease or condition—specifically, the determination of presence or non-presence of elevated LVEDP. The list of the specific features determined to have significant utility in the assessment of the presence or non-presence of abnormal or elevated LVEDP is provided in Table 7.

TABLE 3

| 10 | CV_X_mean    | Mean of X CV     |
|----|--------------|------------------|
| 11 | CV_X_median  | Median of X CV   |
| 12 | CV_X_std*    | Std of X CV      |
| 13 | CV_X_Skew*   | Skewness of X CV |
| 14 | CV_X_Kurt    | Kurtosis of X CV |
| 15 | CV_Y_mean    | Mean of Y CV     |
| 16 | CV_Y_median  | Median of Y CV   |
| 17 | CV_Y_std     | Std of Y CV      |
| 18 | CV_Y_Skew    | Skewness of Y CV |
| 19 | CV_Y_Kurt    | Kurtosis of Y CV |
| 20 | CV_Z_mean    | Mean of Z CV     |
| 21 | CV_Z_median  | Median of Z CV   |
| 22 | CV_Z_std*    | Std of Z CV      |
| 23 | CV_Z_Skew    | Skewness of Z CV |
| 24 | CV_Z_Kurt    | Kurtosis of Z CV |

Figure 10:
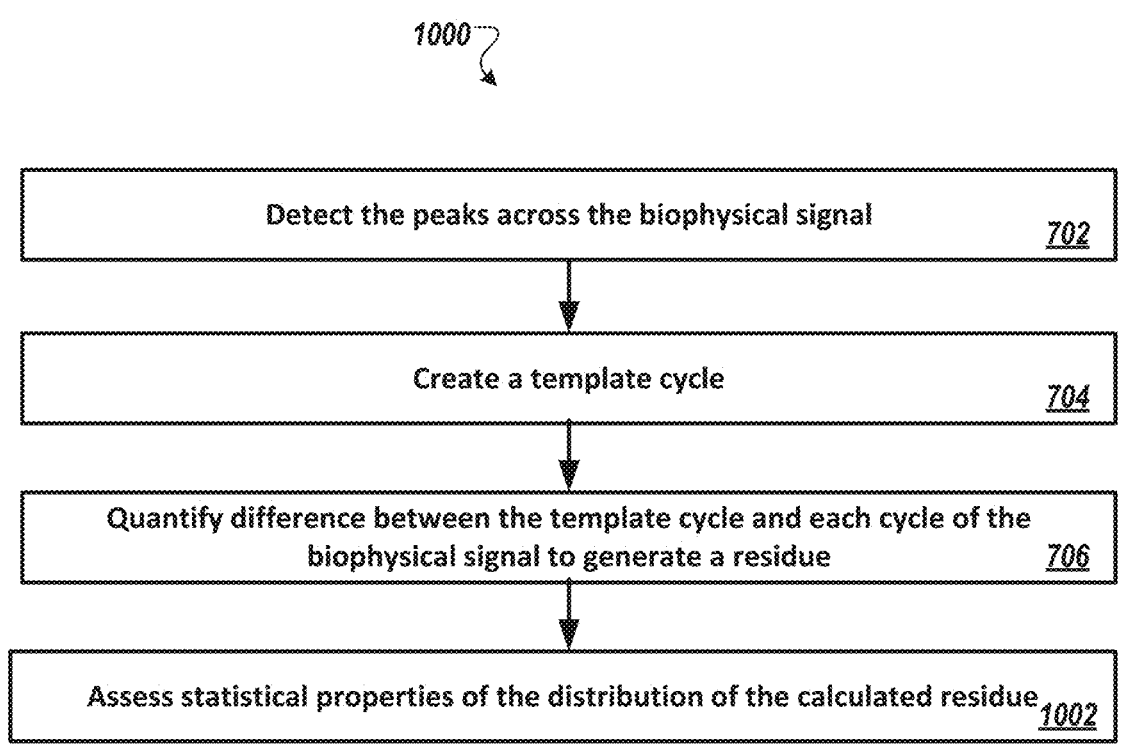
FIG. 10 is a diagram of an exemplary method to generate the cycle variability distribution features for the computation module of FIG. 5 in accordance with an illustrative embodiment.

FIG. 10 is a diagram of an exemplary method 1000 to generate a distribution (e.g., histogram) of cycle-variability residues of a biophysical signal in accordance with an illustrative embodiment. In FIG. 10, Method 1000 may include performing peak detection step (702), a template cycle creation step (704), and a residue distribution calculation step (706) as described in relation to FIG. 7A. Rather than combining all the calculated residue into a single score for the channel, or the set of channels, e.g., as described in relation to FIG. 7A, Method 1000 performs a statistical assessment (1002) of the calculated residue distribution. The distribution can be, e.g., a histogram that includes the calculated CV residue of each cycle of the channel. The statistical assessment may include a mean, median, standard deviation, skewness, and kurtosis of the determined distribution.

Cycle Variability Associated Features Example
3—CV Model Parameters

FIG. 6 illustrates, as a third of three example feature or parameter categories, an example cycle-variability point-cloud analysis feature computation module 600 (shown as "CV Point Cloud Feature(s)" 600) configured to determine values of cycle-variability point-cloud features of one or more acquired biophysical signals in accordance with an illustrative embodiment. In FIG. 6, Module 600 is configured to generate a two- or three-dimensional phase space model (e.g., an alpha shape model) of the calculated CV residue; for example, as described in relation to FIGS. 5, 6, and 7A, and determining geometric-based parameters of that three-dimensional phase space model (e.g., an alpha shape model).

For a cardiac cycle, e.g., with 3 channels, the three-dimensional phase space model can be generated with each channel serving as an axis of the model, or a two-dimensional phase space model can be generated from two channels. The geometric parameters that may be assessed from the three-dimensional phase space model include volume (602), porosity (604), void volume (606), surface area (608). The geometric parameter that may be assessed from the two-dimensional phase space model includes the perimeter (610).

Table 4 shows an example set of cycle-variability features determined from a three-dimensional phase space model and their corresponding description. In Table 4, features (shown designated with "*") have been observed to have significant utility in the assessment of the presence or non-presence of at least one cardiac disease or condition—specifically, the determination of presence or non-presence of elevated LVEDP. The list of the specific features determined to have significant utility in the assessment of the presence or non-presence of abnormal or elevated LVEDP is provided in Table 7.

TABLE 4

| 25 | CV_Volume* | Alpha Shape volume |
|---|---|---|
| 26 | CV_VoidVolume* | CV Convex Hull Volume – CV Alpha Shape Volume |
| 27 | CV_Porosity | $\frac{CV\ Void\ Volume}{CV\ Convex\ Volume}$ |
| 28 | CV_SurfaceArea* | Alpha Shape surface area |
| 29 | CV_PerimeterXY* | Perimeter of the XY Alpha Shape |
| 30 | CV_PerimeterXZ | Perimeter of the XZ Alpha Shape |
| 31 | CV_PerimeterYZ* | Perimeter of the YZ Alpha Shape |

Figure 11:
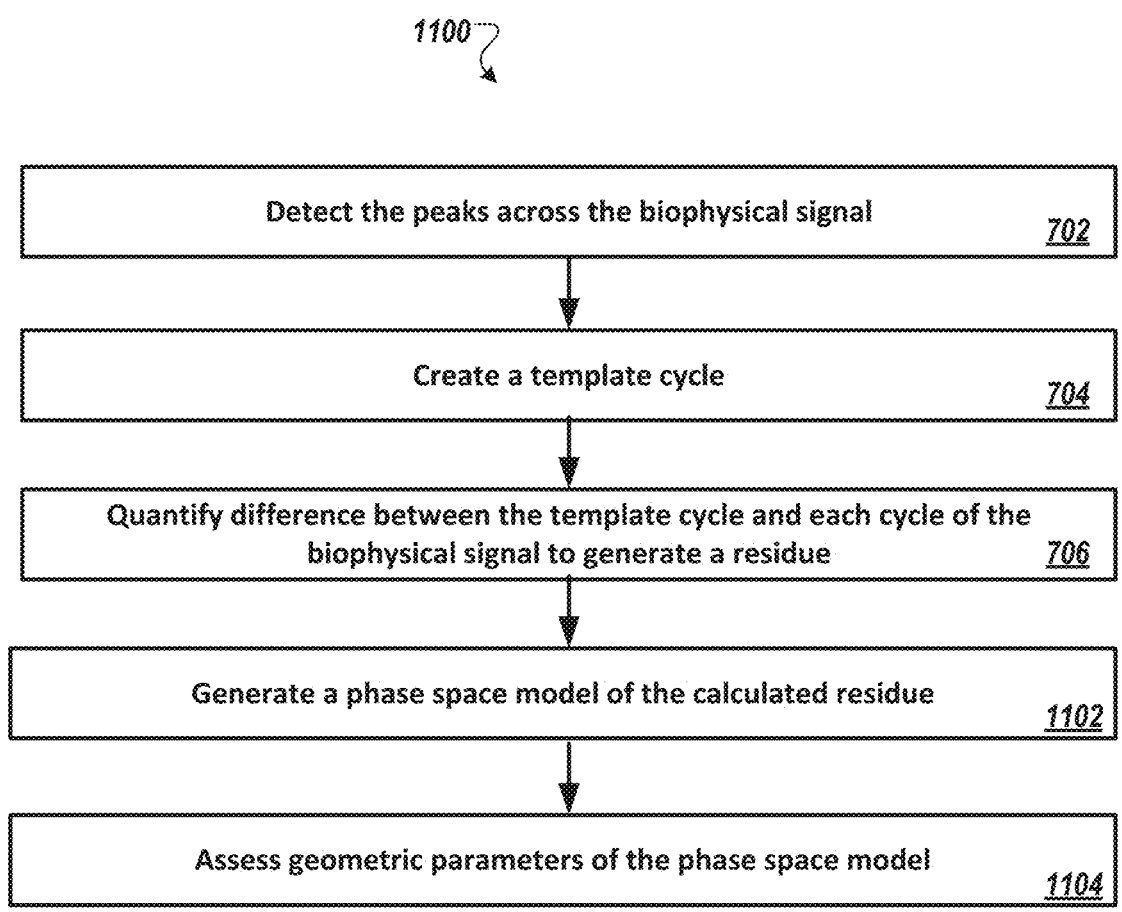
FIG. 11 is a diagram of an exemplary method to generate cycle-variability point-cloud features for the computation module of FIG. 6 in accordance with an illustrative embodiment.

FIG. 11 is a diagram of an exemplary method 1100 to generate a two- or three-dimensional phase space model from the cycle-variability residue of a biophysical signal in accordance with an illustrative embodiment. In FIG. 11, Method 1100 may include performing the peak detection step (702), the template cycle creation step (704), and the residue distribution calculation step (706) as described in relation to FIG. 7A.

Method 1100 further includes generating (1102) a two- or three-dimensional phase space model from the calculated residues determined from the three channels of the acquired data set. The residues may be used generate a point-cloud map to which a triangulation operation may be applied. Examples of triangulation operation include alpha hull as well as convex hull. Other types of triangulation operations may be applied.

FIG. 9C shows an example point-cloud map 906 generated from the residue data set of a three-channel cardiac signal.

Figure 12A:
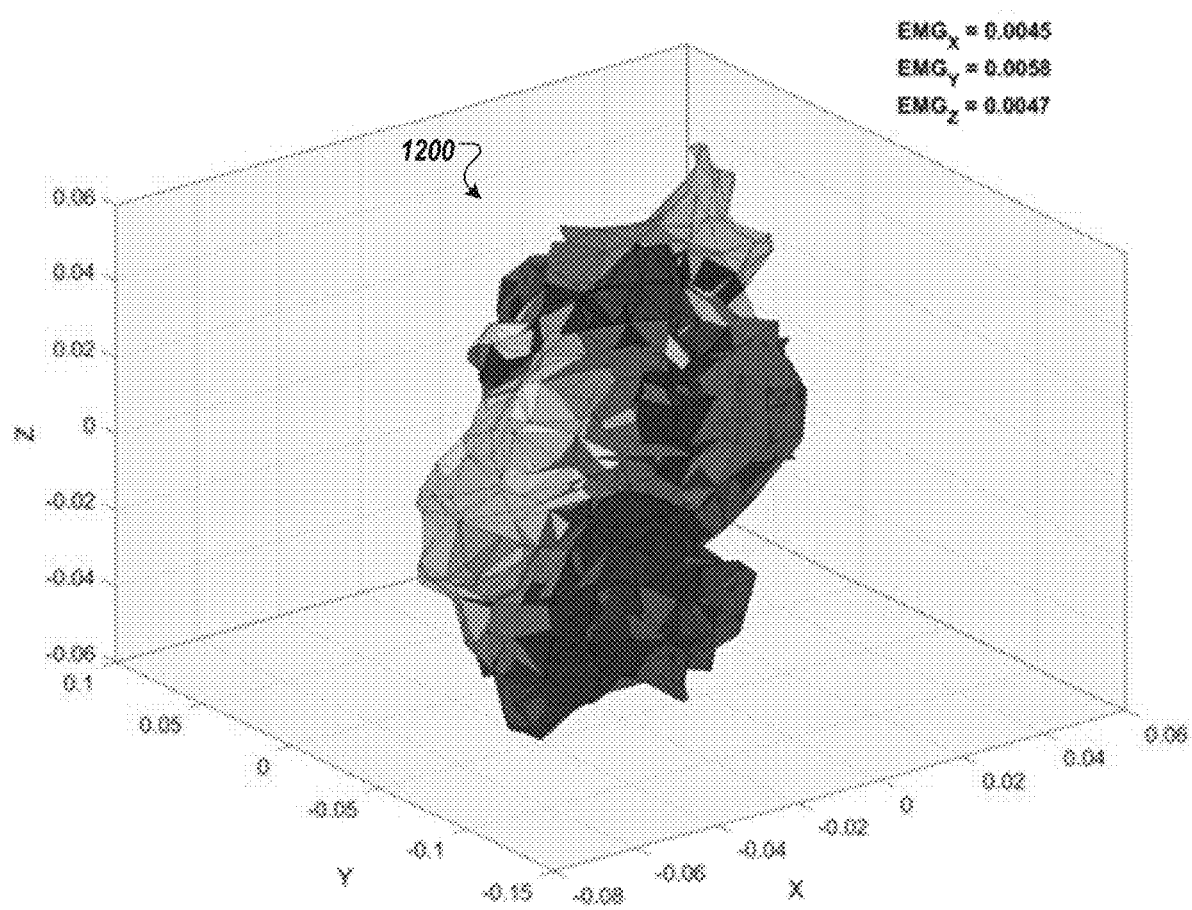
FIG. 12A shows an example three-dimensional phase space model generated by the computation module of FIG. 6 in accordance with an illustrative embodiment.

FIG. 12A shows an example three-dimensional phase space model 1200 generated from the point-cloud map 906 of FIG. 9C in accordance with an illustrative embodiment. The two- or three-dimensional phase space model 1200 may be colorized in some embodiments to assess a fourth-dimensional data. In FIG. 12A, there appears to be a structure in viewing the CV residues in phase space. Further, this structure is related to the temporal location within the cardiac cycle, as can be seen in FIG. 12A in which color can be provided based on the radius components of signals in a spherical coordinate system. For example, as shown in FIG. 12A, there appears to be clustering of high radius amplitudes in certain regions of the image, indicating that the residue in those sections originates from the ventricular depolarization.

Figure 12B:
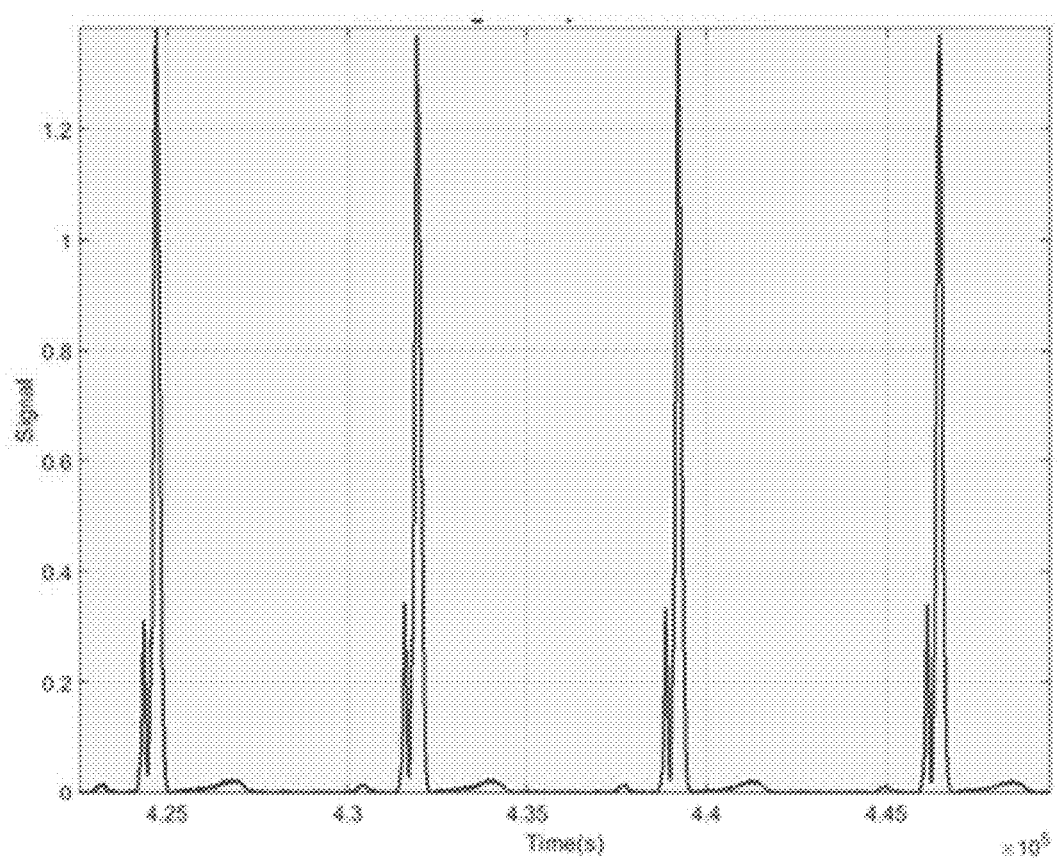
FIG. 12B is a plot illustrating a radius component of a given signal that can be used to colorize the three-dimensional phase space model of FIG. 12A in accordance with an illustrative embodiment.

FIG. 12B is a plot illustrating a radius component of a given signal, in spherical coordinates, in the time domain that can be used to color FIG. 12A. In some embodiments, color information may be used as part of an extracted feature.

Experimental Results and Examples

Several development studies have been conducted to develop feature sets, and in turn, algorithms that can be used to estimate the presence or non-presence, severity, or localization of diseases, medical conditions, or an indication of either. In one study, algorithms were developed for the non-invasive assessment of abnormal or elevated LVEDP. As noted above, abnormal or elevated LVEDP is an indicator of heart failure in its various forms. In another development study, algorithms and features were developed for the non-invasive assessment of coronary artery disease.

As part of these two development studies, clinical data were collected from adult human patients using a biophysical signal capture system and according to protocols described in relation to FIG. 2. The subjects underwent cardiac catheterization (the current "gold standard" tests for CAD and abnormal LVEDP evaluation) following the signal acquisition, and the catheterization results were evaluated for CAD labels and elevated LVEDP values. The collected data were stratified into separate cohorts: one for feature/algorithm development and the other for their validation.

Within the feature development phases, features were developed, including the cycle-variability-related features, to extract characteristics in an analytical framework from biopotential signals (as an example of the cardiac signals discussed herein) and photo-absorption signals (as examples of the hemodynamic or photoplethysmographic discussed herein) that are intended to represent properties of the cardiovascular system. Corresponding classifiers were also developed using classifier models, linear models (e.g., Elastic Net), decision tree models (XGB Classifier, random forest models, etc.), support vector machine models, and neural network models to non-invasively estimate the presence of an elevated or abnormal LVEDP. Univariate feature selection assessments and cross-validation operations were performed to identify features for use in machine learning models (e.g., classifiers) for the specific disease indication of interest. Further description of the machine learning training and assessment are described in a U.S. provisional patent application concurrently filed herewith entitled "Method and System to Non-Invasively Assess Elevated Left Ventricular End-Diastolic Pressure" having 63/235,960, which is hereby incorporated by reference herein in its entirety.

The univariate feature selection assessments evaluated many scenarios, each defined by a negative and a positive dataset pair using t-test, mutual information, and AUC-ROC evaluation. The t-test is a statistical test that can determine if there is a difference between two sample means from two populations with unknown variances. Here, the t-tests were conducted against a null hypothesis that there is no difference between the means of the feature in these groups, e.g., normal LVEDP vs. elevated (for LVEDP algorithm development); CAD− vs. CAD+ (for CAD algorithm development). A small p-value (e.g., ≤0.05) indicates strong evidence against the null hypothesis.

Mutual information (MI) operations were conducted to assess the dependence of elevated or abnormal LVEDP or significant coronary artery disease on certain features. An MI score greater than one indicates a higher dependency between the variables being evaluated. MI scores less than one indicates a lower dependency of such variables, and an MI score of zero indicates no such dependency.

A receiver operating characteristic curve, or ROC curve, illustrates the diagnostic ability of a binary classifier system as its discrimination threshold is varied. The ROC curve may be created by plotting the true positive rate (TPR) against the false positive rate (FPR) at various threshold settings. AUC-ROC quantifies the area under a receiver operating characteristic (ROC) curve—the larger this area, the more diagnostically useful the model is. The ROC, and AUC-ROC, value is considered statistically significant when the bottom end of the 95% confidence interval is greater than 0.50.

Table 6 shows an example list of the negative and a positive dataset pair used in the univariate feature selection assessments. Specifically, Table 6 shows positive datasets being defined as having an LVEDP measurement greater than 20 mmHg or 25 mmHg, and negative datasets were defined as having an LVEDP measurement less than 12 mmHg or belonging to a subject group determined to have normal LVEDP readings.

TABLE 6

| Negative Dataset | Positive Dataset |
|---|---|
| ≤12 (mmHg) | ≥20 (mmHg) |
| ≤12 (mmHg) | ≥25 (mmHg) |
| Normal LVEDP | ≥20 (mmHg) |
| Normal LVEDP | ≥25 (mmHg) |

Tables 7A, 7B, and 7C each shows a list of cycle-variability-related features having been determined to have utility in estimating the presence and non-presence of elevated LVEDP in an algorithm executing in a clinical evaluation system. The features of Tables 7A, 7B, and 7C and corresponding classifiers have been validated to have clinical performance comparable to the gold standard invasive method to measure elevated LVEDP.

TABLE 7

| | FA_scenario LVEDP <= 12 (N = 246) vs >= 20 (N = 209) | | |
|---|---|---|---|
| Feature_name | t-test p-value | AUC (bottom of 95% CI) | MI |
| CV_Z_std | n/s | 0.5184 | 1.0240 |
| CV_PerimeterYZ | 0.0263 | 0.5140 | n/s |
| CV_VoidVolume | n/s | 0.5236 | n/s |
| CV_SurfaceArea | n/s | 0.5352 | n/s |
| CVscore_X. | n/s | 0.5011 | n/s |
| CV_PerimeterXY | n/s | 0.5006 | n/s |
| CV_X_Skew | n/s | 0.5091 | n/s |
| CV_Volume | n/s | 0.5285 | n/s |
| CV_X_std | n/s | 0.5050 | n/s |

The determination that certain cycle-variability-related features have clinical utility in estimating the presence and non-presence of elevated LVEDP provides a basis for the use of these cycle-variability-related features or parameters, as well as other features described herein, in estimating for the presence or non-presence and/or severity and/or localization of other disease, medical condition, or an indication of either particularly, though not limited to, heart disease or conditions described herein.

The experimental results further indicate that intermediary data or parameters of cycle-variability-related features also have clinical utility in diagnostics as well as treatment, controls, monitoring, and tracking applications.

Example Clinical Evaluation System

FIG. 13A shows an example clinical evaluation system 1300 (also referred to as a clinical and diagnostic system) that implements the modules of FIG. 1 to non-invasively compute cycle-variability-related features or parameters, along with other features or parameters, to generate, via a classifier (e.g., machine-learned classifier), one or more metrics associated with the physiological state of a patient or subject according to an embodiment. Indeed, the feature modules (e.g., of FIGS. 1, 5-14) can be generally viewed as a part of a system (e.g., the clinical evaluation system 1300) in which any number and/or types of features may be utilized for a disease state, medical condition, an indication of either, or combination thereof that is of interest, e.g., with different embodiments having different configurations of feature modules. This is additionally illustrated in FIG. 13A, where the clinical evaluation system 1300 is of a modular design in which disease-specific add-on modules 1302 (e.g., to assess for elevated LVEDP or mPAP, CAD, PH/PAH, abnormal LVEF, HFpEF, hypertrophic cardiomyopathy, and others described herein) are capable of being integrated alone or in multiple instances with a singular platform (i.e., a base system 1304) to realize system 1300's full operation. The modularity allows the clinical evaluation system 1300 to be designed to leverage the same synchronously acquired biophysical signals and data set and base platform to assess for the presence of several different diseases as such disease-specific algorithms are developed, thereby reducing testing and certification time and cost.

In various embodiments, different versions of the clinical evaluation system 1300 may implement the assessment system 103 (FIG. 1) by having included containing different feature computation modules that can be configured for a given disease state(s), medical condition(s), or indicating condition(s) of interest. In another embodiment, the clinical evaluation system 1300 may include more than one assessment system 103 and maybe selectively utilized to generate different scores specific to a classifier 116 of that engine 103. In this way, the modules of FIGS. 1 and 13 in a more general sense may be viewed as one configuration of a modular system in which different and/or multiple engines 103, with different and/or multiple corresponding classifiers 116, may be used depending on the configuration of module desired. As such, any number of embodiments of the modules of FIG. 1, with or without the cycle-variability specific feature(s), may exist.

In FIG. 13A, System 1300 can analyze one or more biophysical-signal data sets (e.g., 110) using machine-learned disease-specific algorithms to assess for the likelihood of elevated LVEDP, as one example, of pathology or abnormal state. System 1300 includes hardware and software components that are designed to work together in combination to facilitate the analysis and presentation of an estimation score using the algorithm to allow a physician to use that score, e.g., to assess for the presence or non-presence of a disease state, medical condition, or an indication of either.

The base system 1304 can provide a foundation of functions and instructions upon which each add-on module 1302 (which includes the disease-specific algorithm) then interface to assess for the pathology or indicating condition. The base system 1304, as shown in the example of FIG. 13A, includes a base analytical engine or analyzer 1306, a web-service data transfer API 1308 (shown as "DTAPI" 1308), a report database 1310, a web portal service module 1313, and the data repository 111 (shown as 112*a*).

Data repository 112*a*, which can be cloud-based, stores data from the signal capture system 102 (shown as 102*b*). Biophysical signal capture system 102*b*, in some embodiments, is a reusable device designed as a single unit with a seven-channel lead set and photoplethysmogram (PPG) sensor securely attached (i.e., not removable). Signal capture system 102*b*, together with its hardware, firmware, and software, provides a user interface to collect patient-specific metadata entered therein (e.g., name, gender, date of birth, medical record number, height, and weight, etc.) to synchronously acquire the patient's electrical and hemodynamic signals. The signal capture system 102*b* may securely transmit the metadata and signal data as a single data package directly to the cloud-based data repository. The data repository 112*a*, in some embodiments, is a secure cloud-based database configured to accept and store the patient-specific data package and allow for its retrieval by the analytical engines or analyzer 1306 or 1314.

Base analytical engine or analyzer 1306 is a secure cloud-based processing tool that may perform quality assessments of the acquired signals (performed via "SQA" module 1316), the results of which can be communicated to the user at the point of care. The base analytical engine or analyzer 1306 may also perform pre-processing (shown via pre-processing module 1318) of the acquired biophysical signals (e.g., 110—see FIG. 1). Web portal 1313 is a secure web-based portal designed to provide healthcare providers access to their patient's reports. An example output of the web portal 1313 is shown by visualization 1336. The report databases (RD) 1312 is a secure database and may securely interface and communicate with other systems, such as a hospital or physician-hosted, remotely hosted, or remote electronic health records systems (e.g., Epic, Cerner, Allscrips, CureMD, Kareo, etc.) so that output score(s) (e.g., 118) and related information may be integrated into and saved with the patient's general health record. In some embodiments, web portal 1313 is accessed by a call center to provide the output clinical information over a telephone. Database 1312 may be accessed by other systems that can generate a report to be delivered via the mail, courier service, personal delivery, etc.

Add-on module 1302 includes a second part 1314 (also referred to herein as the analytical engine (AE) or analyzer 1314 and shown as "AE add-on module" 1314) that operates with the base analytical engine (AE) or analyzer 1306. Analytical engine (AE) or analyzer 1314 can include the main function loop of a given disease-specific algorithm, e.g., the feature computation module 1320, the classifier model 1324 (shown as "Ensemble" module 1324), and the outlier assessment and rejection module 1322 (shown as "Outlier Detection" module 1322). In certain modular configurations, the analytical engines or analyzers (e.g., 1306 and 1314) may be implemented in a single analytical engine module.

The main function loop can include instructions to (i) validate the executing environment to ensure all required environment variables values are present and (ii) execute an analysis pipeline that analyzes a new signal capture data file comprising the acquired biophysical signals to calculate the patient's score using the disease-specific algorithm. To execute the analysis pipeline, AE add-on module 1314 can include and execute instructions for the various feature modules 114 and classifier module 116 as described in relation to FIG. 1 to determine an output score (e.g., 118) of the metrics associated with the physiological state of a patient. The analysis pipeline in the AE add-on module 1314 can compute the features or parameters (shown as "Feature Computation" 1320) and identify whether the computed features are outliers (shown as "Outlier Detection" 1322) by providing an outlier detection return for a signal-level response of outlier versus non-outlier based on the feature. The outliers may be assessed with respect to the training data set used to establish the classifier (of module 116). AE add-on module 1314 may generate the patient's output score (e.g., 118) (e.g., via classifier module 1324) using the computed values of the features and classifier models. In the example of an evaluation algorithm for the estimation of elevated LVEDP, the output score (e.g., 118) is an LVEDP score.

The clinical evaluation system 1300 can manage the data within and across components using the web-service DTAPIs 1308 (also may be referred to as HCPP web services in some embodiments). DTAPIs 1308 may be used to retrieve acquired biophysical data sets from, and to store signal quality analysis results to, the data repository 112*a*. DTAPIs 1308 may also be invoked to retrieve and provide the stored biophysical data files to the analytical engines or analyzers (e.g., 1306, 1314), and the results of the analytical engine's analysis of the patient signals may be transferred using DTAPI 1308 to the report database 1310. DTAPIs 1308 may also be used, upon a request by a healthcare professional, to retrieve a given patient data set to the web portal module 1313, which may present a report to the healthcare practitioner for review and interpretation in a secure web-accessible interface.

Clinical evaluation system 1300 includes one or more feature libraries 1326 that store the cycle variability-related features 120 and various other features of the feature modules 122. The feature libraries 1326 may be a part of the add-on modules 1302 (as shown in FIG. 13A) or the base system 1304 (not shown) and are accessed, in some embodiments, by the AE add-on module 1314.

Further details of the modularity of modules and various configurations are provided in a U.S. provisional patent application concurrently filed herewith entitled "Modular Disease Assessment System" having 63/234,772, which is hereby incorporated by reference herein in its entirety.

Example Operation of the Modular Clinical Evaluation System

FIG. 13B shows a schematic diagram of the operation and workflow of the analytical engines or analyzers (e.g., 1306 and 1314) of the clinical evaluation system 1300 of FIG. 13A in accordance with an illustrative embodiment.

Signal quality assessment/rejection (1330). Referring to FIG. 13B, the base analytical engine or analyzer 1306 assesses (1330), via SQA module 1316, the quality of the acquired biophysical-signal data set while the analysis pipeline is executing. The results of the assessment (e.g., pass/fail) are immediately returned to the signal capture system's user interface for reading by the user. Acquired signal data that meet the signal quality requirements are deemed acceptable (i.e., "pass") and further processed and subjected to analysis for the presence of metrics associated with the pathology or indicating condition (e.g., elevated LVEDP or mPAP, CAD, PH/PAH, abnormal LVEF, HFpEF) by the AE add-on module 1314. Acquired signals deemed unacceptable are rejected (e.g., "fail"), and a notification is immediately sent to the user to inform the user to immediately obtain additional signals from the patient (see FIG. 2).

The base analytical engine or analyzer 1306 performs two sets of assessments for signal quality, one for the electrical signals and one for the hemodynamic signals. The electrical signal assessment (1330) confirms that the electrical signals are of sufficient length, that there is a lack of high-frequency noise (e.g., above 170 Hz), and that there is no power line noise from the environment. The hemodynamic signal assessment (1330) confirms that the percentage of outliers in the hemodynamic data set is below a pre-defined threshold and that the percentage and maximum duration that the signals of the hemodynamic data set are railed or saturated is below a pre-defined threshold.

Feature Value Computation (1332). The AE add-on module 1314 performs feature extraction and computation to calculate feature output values. In the example of the LVEDP algorithm, the AE add-on module 1314 determines, in some embodiments, a total of 446 feature outputs belonging to 18 different feature families (e.g., generated in modules 120 and 122), including the cycle variability-related features (e.g., generated in module 120).

Additional descriptions of the various features, including those used in the LVEDP algorithm and other features and their feature families, are described in a US provisional patent application, concurrently filed herewith, entitled "Method and System to Non-Invasively Assess Elevated Left Ventricular End-Diastolic Pressure" having 63/235,960; a US provisional patent application, concurrently filed herewith, entitled "Methods and Systems for Engineering Visual Features From Biophysical Signals for Use in Characterizing Physiological Systems" having 63/236,072; a US provisional patent application, concurrently filed herewith, entitled "Methods and Systems for Engineering Power Spectral Features From Biophysical Signals for Use in Characterizing Physiological Systems" having 63/235,963; a US provisional patent application, concurrently filed herewith, entitled "Method and System for Engineering Rate-Related Features From Biophysical Signals for Use in Characterizing Physiological Systems" having 63/235,966; a U.S. provisional patent application, concurrently filed herewith, entitled "Methods and Systems for Engineering Wavelet-Based Features From Biophysical Signals for Use in Characterizing Physiological Systems" having 63/235,968; a US provisional patent application, concurrently filed herewith, entitled "Methods and Systems for Engineering photoplethysmographic Waveform Features for Use in Characterizing Physiological Systems" having 63/235,971; a US provisional patent application, concurrently filed herewith, entitled "Methods and Systems for Engineering Cardiac Waveform Features From Biophysical Signals for Use in Characterizing Physiological Systems" having 63/236,193; a US provisional patent application, concurrently filed herewith, entitled "Methods and Systems for Engineering Conduction Deviation Features From Biophysical Signals for Use in Characterizing Physiological Systems" having 63/235,974, each of which is hereby incorporated by reference herein in its entirety.

Classifier Output Computation (1334). The AE add-on module 1314 then uses the calculated feature outputs in classifier models (e.g., machine-learned classifier models) to generate a set of model scores. The AE add-on module 1314 joins the set of model scores in an ensemble of the constituent models, which, in some embodiments, averages the output of the classifier models as shown in Equation 6 in the example of the LVEDP algorithm.

$$\text{Ensemble estimation} = \frac{Model_1 + Model_2 + \ldots + Model_n}{n} \quad \text{(Equation 6)}$$

In some embodiments, classifier models may include models that are developed based on ML techniques described in U.S. Patent Publication No. 20190026430, entitled "Discovering Novel Features to Use in Machine Learning Techniques, such as Machine Learning Techniques for Diagnosing Medical Conditions"; or U.S. Patent Publication No. 20190026431, entitled "Discovering Genomes to Use in Machine Learning Techniques," each of which is hereby incorporated by reference herein in its entirety.

In the example of the LVEDP algorithm, thirteen (13) machine-learned classifier models are each calculated using the calculated feature outputs. The 13 classifier models include four ElasticNet machine-learned classifier models [9], four RandomForestClassifier machine-learned classifier models [10], and five extreme gradient boosting (XGB) classifier models [11]. In some embodiments, the patient's metadata information, such as age, gender, BMI value, may be used. The output of the ensemble estimation may be a continuous score. The score may be shifted to a threshold value of zero by subtracting the threshold value for presentation within the web portal. The threshold value may be selected as a trade-off between sensitivity and specificity. The threshold may be defined within the algorithm and used as the determination point for test positive (e.g., "Likely Elevated LVEDP") and test negative (e.g., "Not Likely Elevated LVEDP") condition.

In some embodiments, the analytical engine or analyzer can fuse the set of model scores with a body mass index-based adjustment or an adjustment based on age or gender. For example, the analytical engine or analyzer can average the model estimation with a sigmoid function of the patient BMI having the form $$\text{sigmoid}(x) = \frac{1}{1 + e^{-x}}.$$

Physician Portal Visualization (1336). The patient's report may include a visualization 1336 of the acquired patient data and signals and the results of the disease analyses. The analyses are presented, in some embodiments, in multiple views in the report. In the example shown in FIG. 13B, the visualization 1336 includes a score summary section 1340 (shown as "Patient LVEDP Score Summary" section 1340), a threshold section 1342 (shown as "LVEDP Threshold Statistics" section 1342), and a frequency distribution section 1344 (shown as "Frequency Distribution" section 1308). A healthcare provider, e.g., a physician, can review the report and interpret it to provide a diagnosis of the disease or to generate a treatment plan.

The healthcare portal may list a report for a patient if a given patient's acquired signal data set meets the signal quality standard. The report may indicate a disease-specific result (e.g., elevated LVEDP) being available if the signal analysis could be performed. The patient's estimated score (shown via visual element 118a, 118b, 118c) for the disease-specific analysis may be interpreted relative to an established threshold.

In the score summary section 1340 shown in the example of FIG. 13B, the patient's score 118*a* and associated threshold are superimposed on a two-tone color bar (e.g., shown in section 1340) with the threshold located at the center of the bar with a defined value of "0" representing the delineation between test positive and test negative. The left of the threshold may be lightly shaded light and indicate a negative test result (e.g., "Not Likely Elevated LVEDP") while to the right of the threshold may be darkly shaded to indicate a positive test result (e.g., "Likely Elevated LVEDP").

The threshold section 1342 shows reported statistics of the threshold as provided to a validation population that defines the sensitivity and specificity for the estimation of the patient score (e.g., 118). The threshold is the same for every test regardless of the individual patient's score (e.g., 118), meaning that every score, positive or negative, maybe interpreted for accuracy in view of the provided sensitivity and specificity information. The score may change for a given disease-specific analysis as well with the updating of the clinical evaluation.

The frequency distribution section 1344 illustrates the distribution of all patients in two validation populations (e.g., (i) a non-elevated population to indicate the likelihood of a false positive estimation and (ii) an elevated population to indicate a likelihood of a false negative estimation). The graphs (1346, 1348) are presented as smooth histograms to provide context for interpreting the patient's score 118 (e.g., 118*b*, 118*c*) relative to the test performance validation population patients.

The frequency distribution section 1340 includes a first graph 1346 (shown as "Non-Elevated LVEDP Population" 1346) that shows the score (118*b*), indicating the likelihood of the non-presence of the disease, condition, or indication, within a distribution of a validation population having non-presence of that disease, condition, or indication and a second graph 1348 (shown as "Elevated LVEDP Population" 1348) that shows the store (118*c*), indicates the likelihood of the presence of the disease, condition, or indication, within a distribution of validation population having the presence of that disease, condition, or indication. In the example of the assessment of elevated LVDEP, the first graph 1346 shows a non-elevated LVEDP distribution of the validation population that identifies the true negative (TN) and false positive (FP) areas. The second graph 1348 shows an elevated LVEDP distribution of the validation population that identifies the false negative (TN) and true positive (FP) areas.

The frequency distribution section 1340 also includes interpretative texts of the patient's score relative to other patients in a validation population group (as a percentage). In this example, the patient has an LVEDP score of −0.08, which is located to the left side of the LVEDP threshold, indicating that the patient has "Not Likely Elevated LVEDP."

The report may be presented in the healthcare portal, e.g., to be used by a physician or healthcare provider in their diagnosis for indications of left-heart failure. The indications include, in some embodiments, a probability or a severity score for the presence of a disease, medical condition, or an indication of either.

Outlier Assessment and Rejection Detection (1338). Following the AE add-on module 1314 computing the feature value outputs (in process 1332) and prior to their application to the classifier models (in process 1334), the AE add-on module 1314 is configured in some embodiments to perform outlier analysis (shown in process 1338) of the feature value outputs. Outlier analysis evaluation process 1338 executes a machine-learned outlier detection module (ODM), in some embodiments, to identify and exclude anomalous acquired biophysical signals by identifying and excluding anomalous feature output values in reference to the feature values generated from the validation and training data. The outlier detection module assesses for outliers that present themselves within sparse clusters at isolated regions that are out of distribution from the rest of the observations. Process 1338 can reduce the risk that outlier signals are inappropriately applied to the classifier models and produce inaccurate evaluations to be viewed by the patient or healthcare provider. The accuracy of the outlier module has been verified using hold-out validation sets in which the ODM is able to identify all the labeled outliers in a test set with the acceptable outlier detection rate (ODR) generalization.

While the methods and systems have been described in connection with certain embodiments and specific examples, it is not intended that the scope be limited to the particular embodiments set forth, as the embodiments herein are intended in all respects to be illustrative rather than restrictive. The cycle variability-related features discussed herein may ultimately be employed to make, or to assist a physician or other healthcare provider in making, noninvasive diagnoses or determinations of the presence or non-presence and/or severity of other diseases, medical conditions, or indication of either, such as, e.g., coronary artery disease, pulmonary hypertension and other pathologies as described herein using similar or other development approaches. In addition, the example analysis, including the cycle-variability-related features, can be used in the diagnosis and treatment of other cardiac-related pathologies and indicating conditions as well as neurological-related pathologies and indicating conditions, such assessment can be applied to the diagnosis and treatment (including, surgical, minimally invasive, and/or pharmacologic treatment) of any pathologies or indicating conditions in which a biophysical signal is involved in any relevant system of a living body. One example in the cardiac context is the diagnosis of CAD, and other diseases, medical condition, or indicating conditions disclosed herein and its treatment by any number of therapies, alone or in combination, such as the placement of a stent in a coronary artery, the performance of an atherectomy, angioplasty, prescription of drug therapy, and/or the prescription of exercise, nutritional and other lifestyle changes, etc. Other cardiac-related pathologies or indicating conditions that may be diagnosed include, e.g., arrhythmia, congestive heart failure, valve failure, pulmonary hypertension (e.g., pulmonary arterial hypertension, pulmonary hypertension due to left heart disease, pulmonary hypertension due to lung disease, pulmonary hypertension due to chronic blood clots, and pulmonary hypertension due to other diseases such as blood or other disorders), as well as other cardiac-related pathologies, indicating conditions and/or diseases. Non-limiting examples of neurological-related diseases, pathologies or indicating conditions that may be diagnosed include, e.g., epilepsy, schizophrenia, Parkinson's Disease, Alzheimer's Disease (and all other forms of dementia), autism spectrum (including Asperger syndrome), attention deficit hyperactivity disorder, Huntington's Disease, muscular dystrophy, depression, bipolar disorder, brain/spinal cord tumors (malignant and benign), movement disorders, cognitive impairment, speech impairment, various psychoses, brain/spinal cord/nerve injury, chronic traumatic encephalopathy, cluster headaches, migraine headaches, neuropathy (in its various forms, including peripheral neuropathy), phantom limb/pain, chronic fatigue syndrome, acute and/or chronic pain (including back pain, failed back surgery syndrome, etc.), dyskinesia, anxiety disorders, indicating conditions caused by infections or foreign agents (e.g., Lyme disease, encephalitis, rabies), narcolepsy and other sleep disorders, post-traumatic stress disorder, neurological conditions/effects related to stroke, aneurysms, hemorrhagic injury, etc., tinnitus and other hearing-related diseases/indicating conditions and vision-related diseases/indicating conditions.

In addition, the clinical evaluation system described herein may be configured to analyze biophysical signals such as an electrocardiogram (ECG), electroencephalogram (EEG), gamma synchrony, respiratory function signals, pulse oximetry signals, perfusion data signals; quasi-periodic biological signals, fetal ECG signals, blood pressure signals; cardiac magnetic field signals, heart rate signals, among others.

Further examples of processing that may be used with the exemplified method and system disclosed herein are described in: U.S. Pat. Nos. 9,289,150; 9,655,536; 9,968,275; 8,923,958; 9,408,543; 9,955,883; 9,737,229; 10,039,468; 9,597,021; 9,968,265; 9,910,964; 10,672,518; 10,566,091; 10,566,092; 10,542,897; 10,362,950; 10,292,596; 10,806,349; U.S. Patent Publication nos. 2020/0335217; 2020/0229724; 2019/0214137; 2018/0249960; 2019/0200893; 2019/0384757; 2020/0211713; 2019/0365265; 2020/0205739; 2020/0205745; 2019/0026430; 2019/0026431; PCT Publication nos. WO2017/033164; WO2017/221221; WO2019/130272; WO2018/158749; WO2019/077414; WO2019/130273; WO2019/244043; WO2020/136569; WO2019/234587; WO2020/136570; WO2020/136571; U.S. patent application Ser. Nos. 16/831,264; 16/831,380; 17/132,869; PCT Application nos. PCT/IB2020/052889; PCT/M2020/052890, each of which is hereby incorporated by reference herein in its entirety.

What is claimed is:

1. A method for non-invasively assessing a disease state or a medical condition of a subject, the method comprising:
   obtaining, by one or more processors, a biophysical signal data set of the subject, wherein the biophysical signal data set comprises two or more channels of acquired biopotential signals;
   determining, by the one or more processors, values of cycle variability features or parameters using the biophysical signal data set, wherein the values of the cycle variability features or parameters comprise a cycle variability score determined for each channel of the two or more channels, and each cycle variability score determined for a channel of the two or more channels is normalized by a sum of the cycle variability scores determined for the other channels of the two or more channels; and
   determining, by the one or more processors, an estimated value for a presence of the disease state or the medical condition based in part on an application of the determined values of the cycle variability features or parameters to an estimation model, wherein the estimated value is an estimate of the presence of the disease state or the medical condition for use in a diagnosis of the disease state or the medical condition or to direct treatment of the disease state or the medical condition.

2. The method of claim 1, wherein the step to determining the values of the cycle variability features or parameters comprises:
   determining, by the one or more processors, a template-signal vector data set representing a quasi-periodic signal pattern of the subject from a plurality of detected quasiperiodic cycles detected in the biophysical signal data set; and
   subtracting, by the one or more processors, the template-signal vector data set from two or more of the plurality of detected quasiperiodic cycles to determine values of the cycle variability features.

3. The method of claim 2, wherein at least one value of the values of the cycle variability features is determined as an average of a difference between the template-signal vector data set and each of the two or more of the plurality of detected quasiperiodic cycles.

4. The method of claim 2, wherein at least one value of the cycle variability features or parameters is of a statistical parameter of a distribution of residue values determined between the template-signal vector data and two or more of the plurality of detected quasiperiodic cycles.

5. The method of claim 4, wherein the statistical parameter is a mean, median, standard deviation, skewness, or kurtosis of the distribution.

6. The method of claim 2, wherein the detected quasiperiodic cycles are defined in relation to a landmark determined in the biophysical signal data set.

7. The method of claim 1, wherein the biophysical signal data set comprises the two or more channels of acquired biopotential signals, and wherein at least one value of the cycle variability feature values is determined for each of the two or more channels of acquired biopotential signals.

8. The method of claim 1, wherein the biophysical signal data set comprises the two or more channels of acquired biopotential signals, including a first signal, a second signal, and a third signal, wherein the values of the cycle variability features or parameters are determined as a volume, void volume, porosity, or surface area of a three-dimensional phase space model of a residue generated between a template-signal vector data set and respective first, second, and third signals.

9. The method of claim 8, wherein the three-dimensional phase space model is a triangulation point-cloud model generated from a difference between the template-signal vector data set and the respective first, second, and third signals.

10. The method of claim 1, wherein the estimated value is an estimate of a presence or non-presence of elevated or abnormal left ventricular end-diastolic pressure (LVEDP).

11. The method of claim 1, wherein the disease state, medical condition, or an indication of either is selected from the group consisting of coronary artery disease, pulmonary hypertension, pulmonary arterial hypertension, pulmonary hypertension due to left heart disease, rare disorders that lead to pulmonary hypertension, left ventricular heart failure or left-sided heart failure, right ventricular heart failure or right-sided heart failure, systolic heart failure, diastolic heart failure, ischemic heart disease, hypertrophic cardiomyopathy, and arrhythmia.

12. The method of claim 1 further comprising:
   causing, by the one or more processors, generation of a visualization of the estimated value, wherein the generated visualization is rendered and displayed at a display of a computing device and/or presented in a report.

13. The method of claim 1, wherein values of one or more cycle variability associated properties are used in the model selected from the group consisting of a linear model, a decision tree model, a random forest model, a support vector machine model, a neural network model.

14. The method of claim 13, wherein the model further includes features selected from the group consisting of:
- one or more depolarization or repolarization wave propagation associated features;
- one or more depolarization wave propagation deviation associated features;
- one or more cycle variability associated features;
- one or more dynamical system associated features;
- one or more cardiac waveform topologic and variations associated features;
- one or more PPG waveform topologic and variations associated features;
- one or more cardiac or PPG signal power spectral density associated features;
- one or more cardiac or PPG signal visual associated features; and
- one or more predictability features.

15. The method of claim 1, further comprising:
acquiring, by one or more acquisition circuits of a measurement system, voltage gradient signals, wherein the voltage gradient signals are acquired at a frequency greater than about 1 kHz; and
generating, by the one or more acquisition circuits, the obtained biophysical data set from the acquired voltage gradient signals.

16. The method of claim 1, further comprising:
acquiring, by one or more acquisition circuits of a measurement system, one or more photoplethysmographic signals; and
generating, by the one or more acquisition circuits, the obtained biophysical data set from the acquired voltage gradient signals.

17. A system comprising:
a processor; and
a memory having instructions stored thereon, wherein execution of the instructions by the processor causes the processor to:
obtain a biophysical signal data set of a subject, wherein the biophysical signal data set comprises two or more channels of acquired biopotential signals;
determine values of cycle variability features or parameters using the biophysical signal data set, wherein the values of the cycle variability features or parameters comprise a cycle variability score determined for each channel of the two or more channels, and each cycle variability score determined for a channel of the two or more channels is normalized by a sum of the cycle variability scores determined for the other channels of the two or more channels; and
determine an estimated value for a presence of a disease state or a medical condition based in part on an application of the determined values of the cycle variability features or parameters to an estimation model, wherein the estimated value is an estimate of the presence of the disease state or the medical condition for use in a diagnosis of the disease state or the medical condition or to direct treatment of the disease state or the medical condition.

18. A non-transitory computer-readable medium having instructions stored thereon, wherein execution of the instructions by a processor causes the processor to:
obtain a biophysical signal data set of a subject, wherein the biophysical signal data set comprises two or more channels of acquired biopotential signals;
determine values of cycle variability features or parameters using the biophysical signal data set, wherein the values of the cycle variability features or parameters comprise a cycle variability score determined for each channel of the two or more channels, and each cycle variability score determined for a channel of the two or more channels is normalized by a sum of the cycle variability scores determined for the other channels of the two or more channels; and
determine an estimated value for a presence of a disease state or a medical condition based in part on an application of the determined values of the cycle variability features or parameters to an estimation model, wherein the estimated value is an estimate the presence of the disease state or the medical condition for use in a diagnosis of the disease state or the medical condition or to direct treatment of the disease state or the medical condition.

* * * * *